United States Patent
Nakai et al.

(10) Patent No.: US 9,958,376 B2
(45) Date of Patent: May 1, 2018

(54) FLOATING PARTICLE DETECTION DEVICE

(71) Applicant: MITSUBISHI ELECTRIC CORPORATION, Tokyo (JP)

(72) Inventors: Kenya Nakai, Tokyo (JP); Nobuo Takeshita, Tokyo (JP)

(73) Assignee: Mitsubishi Electric Corporation, Tokyo (JP)

( * ) Notice: Subject to any disclaimer, the term of this patent is extended or adjusted under 35 U.S.C. 154(b) by 43 days.

(21) Appl. No.: 15/302,949

(22) PCT Filed: Feb. 19, 2015

(86) PCT No.: PCT/JP2015/054520
§ 371 (c)(1),
(2) Date: Oct. 7, 2016

(87) PCT Pub. No.: WO2015/156037
PCT Pub. Date: Oct. 15, 2015

(65) Prior Publication Data
US 2017/0038290 A1    Feb. 9, 2017

(30) Foreign Application Priority Data

Apr. 8, 2014   (JP) .................... 2014-079279

(51) Int. Cl.
*G01N 15/02* (2006.01)
*G01N 21/49* (2006.01)
(Continued)

(52) U.S. Cl.
CPC ..... *G01N 15/1434* (2013.01); *G01N 15/0211* (2013.01); *G01N 15/06* (2013.01);
(Continued)

(58) Field of Classification Search
None
See application file for complete search history.

(56) References Cited

U.S. PATENT DOCUMENTS 3,723,007 A * 3/1973 Leonard ............... G01J 3/44
356/301
3,915,572 A * 10/1975 Orloff ................... G01P 5/26
356/28

(Continued)

FOREIGN PATENT DOCUMENTS

JP    63-113345 A    5/1988
JP    4-6436 A       1/1992

(Continued)

OTHER PUBLICATIONS

Hiromoto et al., "Asbestos real-time monitor in an atmospheric environment", Applied Optics, Dec. 20, 1997, vol. 36, No. 36, pp. 9475-9480.

(Continued)

*Primary Examiner* — Shawn DeCenzo
*Assistant Examiner* — Jarreas C. Underwood
(74) *Attorney, Agent, or Firm* — Birch, Stewart, Kolasch & Birch, LLP

(57) ABSTRACT

A floating particle detection device 1 is capable of accurately identifying the type of a floating particle while achieving simplification of a configuration of the device, the device includes: a laser light irradiator (10) that includes a laser light emitting element (11) and a back-monitor-use light receiving element (12); a scattered light receiver (20) that selectively receives light of a predetermined polarization component among scattered light generated when a floating particle (50) is irradiated and that generates a second detection signal; and an identification processor (30) that identifies the type of the floating particle on the basis of a first detection signal and the second detection signal. Incident light entering the back-monitor-use light receiving element (12) includes: a back-monitor-use laser beam (L0); and (Continued)

backscattered light (Lbs) travelling toward the laser light irradiator (10) among the scattered light (Ls).

20 Claims, 15 Drawing Sheets

(51) Int. Cl.
| | | |
|---|---|---|
| *G01S 7/499* | (2006.01) | |
| *G01S 17/95* | (2006.01) | |
| *G01N 15/14* | (2006.01) | |
| *G01N 15/06* | (2006.01) | |
| *G01N 21/53* | (2006.01) | |
| *H01S 5/00* | (2006.01) | |
| *H01S 5/0683* | (2006.01) | |
| *G01S 7/491* | (2006.01) | |
| G01N 15/00 | (2006.01) | |
| H01S 5/042 | (2006.01) | |
| H01S 5/06 | (2006.01) | |

(52) U.S. Cl.
CPC ............ *G01N 21/49* (2013.01); *G01N 21/53* (2013.01); *G01S 7/499* (2013.01); *G01S 7/4916* (2013.01); *G01S 17/95* (2013.01); *H01S 5/0028* (2013.01); *H01S 5/06832* (2013.01); *G01N 2015/0046* (2013.01); *G01N 2015/0693* (2013.01); *G01N 2015/1454* (2013.01); *G01N 2201/0683* (2013.01); *G01N 2201/06113* (2013.01); *H01S 5/0427* (2013.01); *H01S 5/0617* (2013.01)

(56) References Cited

U.S. PATENT DOCUMENTS

| | | | | |
|---|---|---|---|---|
| 3,966,324 | A | * | 6/1976 | Iten ........................ G01P 5/26 356/28 |
| 4,026,655 | A | * | 5/1977 | Gunter, Jr. .............. G01P 3/366 250/574 |
| 4,359,640 | A | * | 11/1982 | Geiger .................... G01S 17/95 250/372 |
| 5,017,497 | A | | 5/1991 | de Grooth et al. |
| 5,192,870 | A | * | 3/1993 | Batchelder ......... G01N 15/0205 250/574 |
| 7,495,774 | B2 | * | 2/2009 | Hays ...................... G01N 21/47 356/519 |
| 8,009,290 | B2 | | 8/2011 | Unger |
| 8,072,584 | B2 | * | 12/2011 | Caldwell .................. F03D 7/02 356/28.5 |
| 2008/0218738 | A1 | | 9/2008 | Trainer |

FOREIGN PATENT DOCUMENTS

| | | |
|---|---|---|
| JP | 5-264434 A | 10/1993 |
| JP | 6-241975 A | 9/1994 |
| JP | 7-83819 A | 3/1995 |
| JP | 11-44628 A | 2/1999 |
| JP | 2003-28777 A | 1/2003 |
| JP | 2006-138727 A | 6/2006 |
| JP | 3850418 B2 | 11/2006 |
| JP | 2008-241361 A | 10/2008 |

OTHER PUBLICATIONS

Meigas, "Method for small particle detection by laser," Opt. Eng., vol. 37, No. 9, Sep. 1998, XP000789027, pp. 2587-2591.

* cited by examiner

FIG. 5

| | IRREGULAR SHAPE | SPHERICAL SHAPE |
|---|---|---|
| L1 | A — LINEAR POLARIZATION (vertical along y) | B — LINEAR POLARIZATION (vertical along y) |
| Ls | C — diagonal arrow | D — vertical arrow along y |
| COMPONENT ORTHOGONAL TO POLARIZATION DIRECTION OF L1 | E — horizontal arrow along x | F — (none) |
| COMPONENT IN THE SAME DIRECTION AS POLARIZATION DIRECTION OF L1 | G — vertical arrow along y | H — vertical arrow along y |

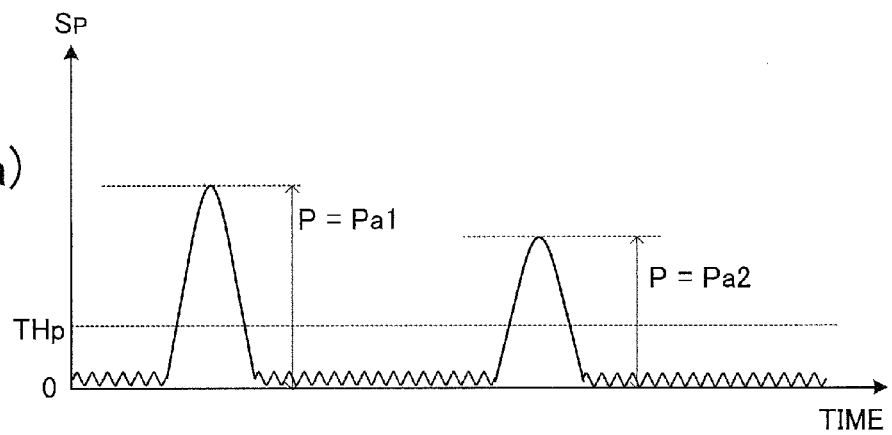
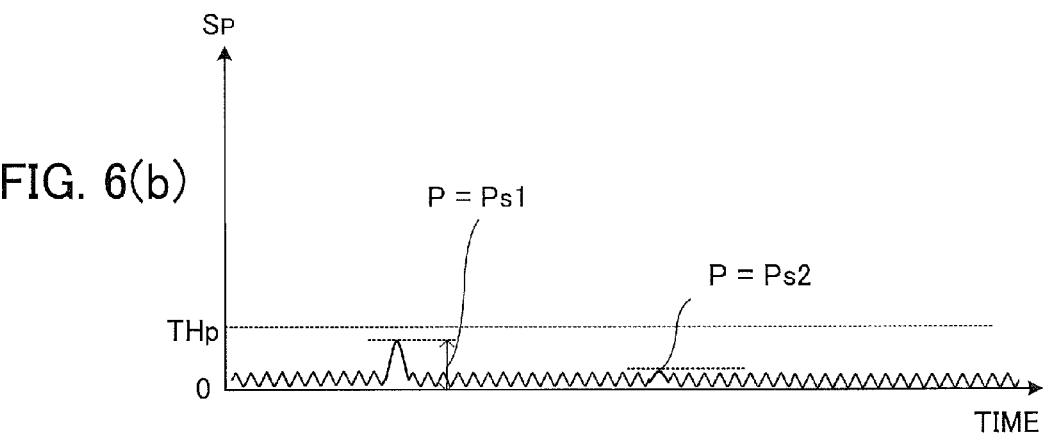

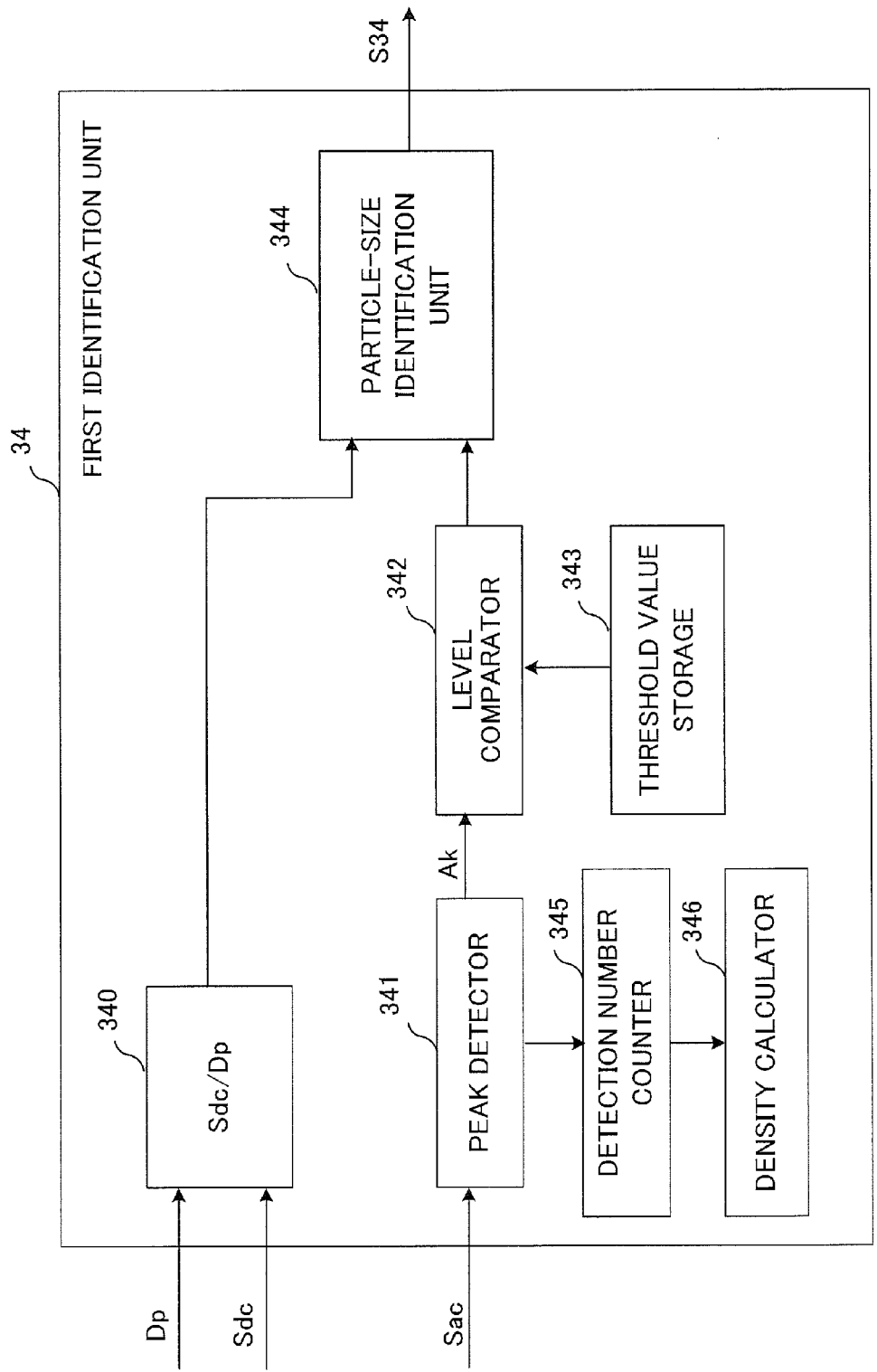

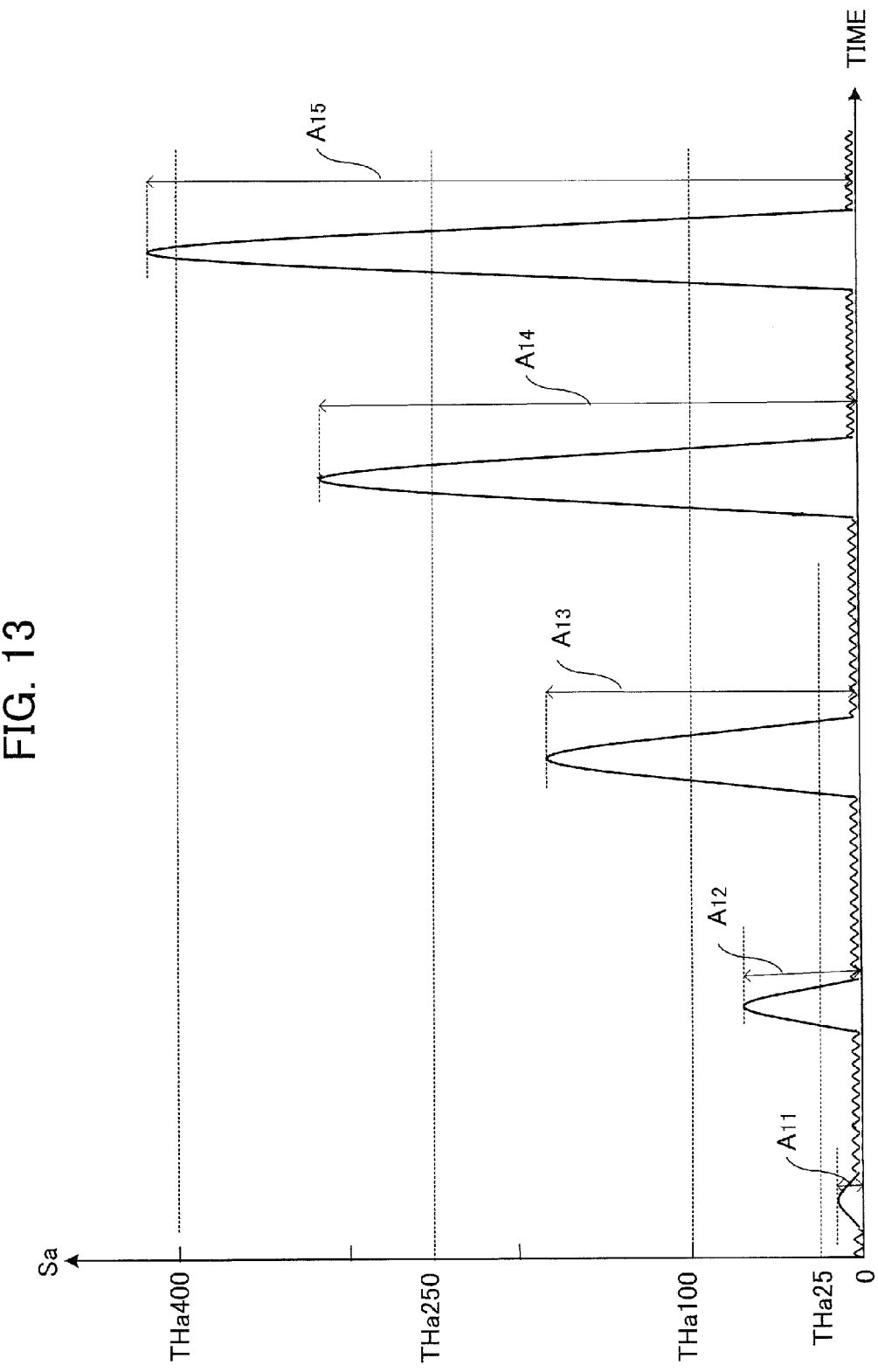

FIG. 14

| OUTPUT INFORMATION S34 OF FIRST IDENTIFICATION UNIT | | OUTPUT INFORMATION S35 OF SECOND IDENTIFICATION UNIT | | OUTPUT INFORMATION S36 OF THIRD IDENTIFICATION UNIT |
|---|---|---|---|---|
| IDENTIFICATION | SIZE OF PARTICLE | IDENTIFICATION | SHAPE OF PARTICLE | TYPE IDENTIFICATION |
| $Sdc / Dp > THc$ | ~ 0.5 $\mu m$ | — | — | CIGARETTE SMOKE |
| $An \leqq THa25$ | 0.5 $\mu m$ ~ 2.5 $\mu m$ | — | — | PM2.5 |
| $THa25 < An \leqq THa100$ | 2.5 $\mu m$ ~ 10 $\mu m$ | — | — | PM10 |
| $THa100 < An \leqq THa250$ | 10 $\mu m$ ~ 25 $\mu m$ | $P \leqq THp$ | SPHERICAL SHAPE | POLLEN |
| $THa100 < An \leqq THa250$ | 10 $\mu m$ ~ 25 $\mu m$ | $THp < P$ | IRREGULAR SHAPE | HOUSE DUST |
| $THa250 < An \leqq THa400$ | 25 $\mu m$ ~ 40 $\mu m$ | $P \leqq THp$ | SPHERICAL SHAPE | POLLEN |
| $THa250 < An \leqq THa400$ | 25 $\mu m$ ~ 40 $\mu m$ | $THp < P$ | IRREGULAR SHAPE | HOUSE DUST |
| $THa400 < An$ | 40 $\mu m$ ~ | — | — | HOUSE DUST |

FLOATING PARTICLE DETECTION DEVICE

TECHNICAL FIELD

The present invention relates to a floating particle detection device that has a function of identifying a type of a floating particle.

BACKGROUND ART

Various floating particle detection devices for detecting scattered light generated when a space in which floating microscopic particulate matter (hereinafter referred to as 'floating particles'), such as pollen and dust, is present is irradiated with light, and performing detection or identification of a quantity of the floating particles, size of the floating particle, or a type of the floating particle have been proposed.

For example, patent document 1 describes a pollen sensor that distinguishes between pollen and soil dust and that includes: a light emitting means for emitting a laser beam in a horizontal direction toward a detection-target region; a first light receiving means disposed in a position at an angle of 60° obliquely upward from the center position of the detection-target region with reference to the horizontal direction; and a second light receiving means disposed in a position at an angle of 60° obliquely downward from the center position of the detection-target region with reference to the horizontal direction.

Patent document 2 describes a particle sensor that includes a semiconductor laser and a light receiving element and that converts a laser beam radiated from the semiconductor laser to a substantially parallel light flux with a lens, detects scattered light generated when a floating particle is irradiated with the laser beam of the parallel light flux with the light receiving element, and thus performs detection of a quantity of the floating particles and identification of size of the floating particle.

PRIOR ART REFERENCE

Patent Document

Patent Document 1: Japanese Patent No. 3850418 (for example, paragraphs 0013 to 0023, FIG. 1, FIG. 4)
Patent Document 2: U.S. Pat. No. 8,009,290 (for example, FIG. 5)

SUMMARY OF THE INVENTION

Problem to be Solved by the Invention

However, the pollen sensor described in patent document 1 includes the two light receiving means in a positional relationship of symmetry with reference to the horizontal direction which is a travel direction of the laser beam, i.e., the first light receiving means and second light receiving means, and each of the first light receiving means and second light receiving means includes a lens and a light reception sensor. Thus, in the pollen sensor described in patent document 1, there are problems that the number of components increases, the configuration of the device is complicated and the device increases in size.

As to the particle sensor described in patent document 2, since a component of a detector of the scattered light is only the single light receiving element, it is conceivable that the number of the floating particles and the size of the floating particle can be identified, but there is a problem that a type of the floating particle cannot be accurately identified.

Therefore, the present invention is made to solve the above problems of the conventional art, and an object of the present invention is to provide a floating particle detection device capable of accurately identifying a type of a floating particle while it achieves simplification of a configuration of the device.

Means for Solving the Problem

The floating particle detection device according to one aspect of the present invention includes: a laser light irradiator that includes a laser light emitting element including a front-side edge surface that emits an irradiation laser beam with which a detection-target region where floating particles are present is irradiated and a back-side edge surface that emits a back-monitor-use laser beam which travels in a direction opposite to a travel direction of the irradiation laser beam, and a back-monitor-use light receiving element disposed in a position where the back-monitor-use laser beam is incident, the back-monitor-use light receiving element generating a first detection signal according to an amount of incident light; a scattered light receiver that selectively receives light of a predetermined polarization component among scattered light of the irradiation laser beam, the scattered light being generated when a floating particle is irradiated, thereby generating a second detection signal; and an identification processor that identifies a type of the floating particle on a basis of the first detection signal and the second detection signal. The incident light entering the back-monitor-use light receiving element includes the back-monitor-use laser beam and backscattered light travelling toward the laser light irradiator among the scattered light of the irradiation laser beam with which the floating particle is irradiated.

The floating particle detection device according to another aspect of the present invention includes: a laser light irradiator that includes a laser light emitting element including a front-side edge surface that emits an irradiation laser beam with which a detection-target region where floating particles are present is irradiated and a back-side edge surface that emits a back-monitor-use laser beam which travels in a direction opposite to a travel direction of the irradiation laser beam, and a back-monitor-use light receiving element disposed in a position where the back-monitor-use laser beam is incident, the back-monitor-use light receiving element generating a first detection signal according to an amount of incident light; a scattered light receiver that selectively receives light of a predetermined polarization component among scattered light of the irradiation laser beam, the scattered light being generated when a floating particle is irradiated, thereby generating a second detection signal; and an identification processor that identifies a type of the floating particle on a basis of the first detection signal and the second detection signal. A fluctuation of the back-monitor-use laser beam is used for the identification of the type of the floating particle. The fluctuation is caused by entering of backscattered light travelling toward the laser light irradiator, among the scattered light of the irradiation laser beam with which the floating particle is irradiated, through the front-side edge surface of the laser light emitting element of the laser light irradiator.

Effects of the Invention

Thus, according to the present invention, it is possible to accurately identify a type of a floating particle while simplification of a configuration of the device is achieved.

BRIEF DESCRIPTION OF THE DRAWINGS

FIG. 5 is a diagram in which parts A and B show polarization directions of an irradiation laser beam with which irregular-shaped and spherical-shaped floating particles are irradiated in the floating particle detection device according to the first embodiment with double-headed arrows on a plane perpendicular to an optical axis; parts C and D show polarization directions of scattered light generated when the irregular-shaped and spherical-shaped floating particles are irradiated with the irradiation laser beam with double-headed arrows on the plane perpendicular to the optical axis; parts E and F show polarization components of the scattered light in the direction which is orthogonal to the polarization direction of the irradiation laser beam; and parts G and H show polarization components of the scattered light in the same direction as the polarization direction of the irradiation laser beam.

FIG. 6(a) is a diagram schematically showing an example of a detection waveform when a scattered light receiving element in a scattered light receiver of the floating particle detection device according to the first embodiment detects scattered light from an irregular-shaped particle; FIG. 6(b) is a diagram schematically showing an example of a detection waveform when the scattered light receiving element in the scattered light receiver of the floating particle detection device according to the first embodiment detects scattered light from a spherical-shaped particle.

FIG. 11 is a block diagram showing internal processing of a first identification unit.

FIG. 13 is a diagram schematically showing relationship between threshold values and waveforms of the alternating-current component generated by the direct-current/alternating-current separator in the floating particle detection device according to the first embodiment.

FIG. 14 is a diagram showing an example of identification of types of floating particles according to combinations of floating-particle shapes and floating-particle sizes by a third identification unit in the floating particle detection device according to the first embodiment.

MODE FOR CARRYING OUT THE INVENTION

First Embodiment

Figure 1:
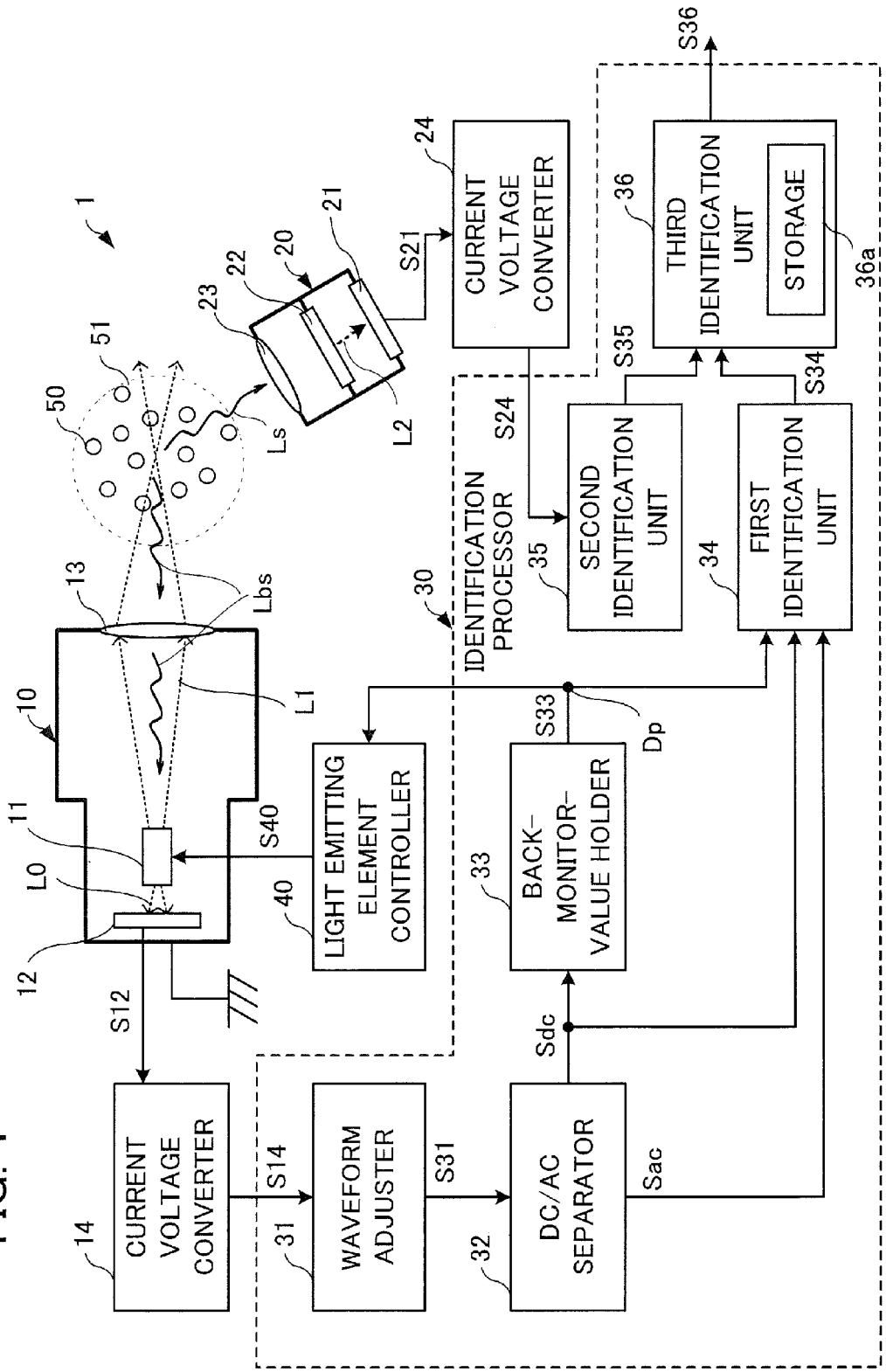
FIG. 1 is a diagram schematically showing a configuration of a floating particle detection device according to a first embodiment of the present invention.

FIG. 1 is a diagram schematically showing a configuration of a floating particle detection device 1 according to a first embodiment of the present invention. As shown in FIG. 1, the floating particle detection device 1 according to the first embodiment includes, as main components, a laser light irradiator 10, a scattered light receiver 20 and an identification processor 30. The floating particle detection device 1 can also include a light emitting element controller 40. The floating particle detection device 1 according to the first embodiment has a function of identifying a type of a floating particle 50 suspended in a detection-target region 51, i.e., in space. In other words, the floating particle detection device 1 has a function of identifying the type of the floating particle 50 suspended in the space of the detection-target region 51. The detection-target region 51 may be a region in a gas such as air, a region in a liquid such as water, or a vacuum region. The detection-target region 51 may be a region in a flow path where a gas or liquid flows or in a container. Further, the detection-target region 51 may be a closed region such as the inside of a room or an open region such as the outside of a building. There is no special limitation on the floating particle 50 which is a detection target, if it is microscopic matter which generates scattered light when it is irradiated with irradiation light. The irradiation light is a laser beam or the like, for example. In the following description, the irradiation light is a laser beam. Typical examples of the floating particles 50 which are the detection targets are pollen, dead bodies and droppings of minute organisms such as mites, dust called house dust, cigarette smoke, microscopic particulate matter PM2.5 and PM10, and so on. That is, the floating particles 50 which are the detection targets include pollen, dust called house dust, cigarette smoke and so on. The floating particles 50 which are the detection targets also include dead bodies and droppings of minute organisms such as mites. The floating particles 50 which are the detection targets also include microscopic particulate matter PM2.5, microscopic particulate matter PM10 and so on. In addition, 'scattered light' in the present application is light generated when the irradiation laser beam L1 strikes a floating particle and thus changes its propagation state. However, 'scattered light' in the present application also includes floating particle's fluorescence which occurs due to the wavelength of the irradiation laser beam L1.

As shown in FIG. 1, the laser light irradiator 10 includes a laser light emitting element 11 and a back-monitor-use light receiving element 12. The laser light irradiator 10 can include a condenser lens 13. The back-monitor-use light receiving element 12 is arranged in a position where it can detect the intensity of a laser beam emitted from the laser light emitting element 11. The laser light irradiator 10 is a semiconductor laser element or a semiconductor laser irradiation device. The laser light irradiator 10 may be an optical component or an optical unit which is generally marketed.

The laser light emitting element 11 is a semiconductor laser chip. The laser light emitting element 11 emits an irradiation laser beam L1 with which the detection-target region 51 where the floating particles 50 are present is irradiated, from a front-side edge surface (an edge surface on the right side in FIG. 1). The laser light emitting element 11 emits a back-monitor-use laser beam L0 which travels in a direction opposite to a travel direction of the irradiation laser beam L1, from a back-side edge surface (an edge surface on the left side in FIG. 1).

The condenser lens 13 concentrates the irradiation laser beam L1 emitted from the laser light emitting element 11, within the detection-target region 51 where the floating particles 50 are present. In a case where the intensity of the irradiation laser beam L1 can be set to be sufficiently large for detection of the floating particle 50 and suchlike cases, it is possible to omit the condenser lens 13.

The back-monitor-use light receiving element 12 is arranged in a position where the back-monitor-use laser beam L0 enters. A light reception surface of the back-monitor-use light receiving element 12 faces the back-side edge surface of the laser light emitting element 11. Accordingly, the light reception surface of the back-monitor-use light receiving element 12 also faces the detection-target region 51. The back-monitor-use light receiving element 12 outputs a current signal S12 according to an amount of incident light. The incident light which enters the back-monitor-use light receiving element 12 includes: the back-monitor-use laser beam L0 which is emitted from the laser light emitting element 11; and backscattered light Lbs from the floating particle 50 which is irradiated with the irradiation laser beam L1.

A current voltage converter 14 shown in FIG. 1 is supplied with the current signal S12 from the back-monitor-use light receiving element 12. The current voltage converter 14 converts the current signal S12 to a voltage signal S14 which corresponds to the current signal S12. The current voltage converter 14 supplies the voltage signal S14 to the identification processor 30. In some products, the back-monitor-use light receiving element 12 has the function of the current voltage converter 14. In that case, there is no need to provide the current voltage converter 14. In general, light the amount of which is proportional to emission power of the irradiation laser beam L1 enters the back-monitor-use light receiving element 12.

For this reason, it is general for an output signal of the back-monitor-use light receiving element 12 to be used for monitoring power of the irradiation laser beam L1 emitted from the front-side edge surface of the laser light emitting element 11. The floating particle detection device 1 according to the first embodiment also uses the back-monitor-use light receiving element 12 for detecting the backscattered light Lbs from the floating particle 50. The backscattered light Lbs is scattered light obtained when the floating particle 50 is irradiated with the irradiation laser beam L1. In this regard, the floating particle detection device 1 adopts the use which is different from the general use of the back-monitor-use light receiving element.

As shown in FIG. 1, the scattered light receiver 20 includes a scattered light detection element 21, a polarizing filter 22 and a lens 23. The scattered light detection element 21 can detect at least light in the wavelength band of the irradiation laser beam L1. The scattered light detection element 21 is arranged in a position through which light transmitted through the polarizing filter 22 enters. The scattered light detection element 21 outputs a current signal S21 according to an amount of incident light. The polarizing filter 22 has a function as a polarizing member. The polarizing filter 22 selectively transmits light in a polarization direction of a predetermined one direction (i.e., a polarization component in one direction) L2, among scattered light Ls of the irradiation laser beam L1 with which the floating particle 50 is irradiated. In the first embodiment, light in the polarization direction transmitted through the polarizing filter 22 among the scattered light Ls is light having the polarization direction which is orthogonal to a polarization direction of the irradiation laser beam L1. The lens 23 concentrates the scattered light Ls onto the scattered light detection element 21. If the scattered light Ls enough for the detection is received, the lens 23 can be omitted.

A current voltage converter 24 converts the input current signal S21 to a voltage signal. The current voltage converter 24 supplies the voltage signal S24 to the identification processor 30. In some products, the scattered light detection element 21 has the function of the current voltage converter 24. In that case, there is no need to provide the current voltage converter 24.

As shown in FIG. 1, the identification processor 30 includes a direct-current/alternating-current (DC/AC) separator 32, a back-monitor-value holder 33, a first identification unit 34, a second identification unit 35 and a third identification unit 36. The identification processor 30 can also include a waveform adjuster 31.

The waveform adjuster 31 has an equalizer capable of changing a gain according to frequency, for example. The waveform adjuster 31 adjusts a waveform of the first detection signal S14, for example, so as to emphasize an alternating-current component which corresponds to the backscattered light Lbs more than a direct-current component which corresponds to the back-monitor-use laser beam L0. The waveform of the first detection signal S14 is a waveform obtained by converting the current signal S12 generated by the back-monitor-use light receiving element 12 into the voltage signal. The waveform adjuster 31 supplies the DC/AC separator 32 with a second detection signal S31 obtained by adjusting the waveform of the first detection signal S14. The waveform adjuster 31 improves the quality of processing at subsequent processors. However, the waveform adjuster 31 is not an essential component and can be omitted.

The DC/AC separator 32 separates the detection signal S31 into a direct-current component signal Sdc and an alternating-current component signal Sac. The detection signal S31 is a signal based on a detection value of the back-monitor-use light receiving element 12. The direct-current component signal Sdc is a direct-current component which corresponds to the back-monitor-use laser beam L0. The alternating-current component signal Sac is an alternating-current component which corresponds to the backscattered light Lbs. In the example of FIG. 1, the DC/AC separator 32 receives the adjusted detection signal S31 which is supplied from the waveform adjuster 31. The DC/AC separator 32 separates the alternating-current (AC) component signal Sac of the detection signal S31 and the direct-current (DC) component signal Sdc of the detection signal S31. The DC-component signal Sdc is supplied to the back-monitor-value holder 33 and the first identification unit 34. The AC-component signal Sac is supplied to the first identification unit 34. A value of the DC-component signal Sdc generated by the DC/AC separator 32 is a value which corresponds to a mean value of the intensity of the laser beam L0. The mean value of the intensity of the laser beam L0 corresponds to a mean value of the intensity of the laser beam L1. The laser beam L1 is a laser beam emitted from the laser light emitting element 11 toward the floating particles 50 of measurement targets. A value of the AC-component signal Sac of the detection signal is a value which corresponds to the intensity of the backscattered light Lbs among the scattered light Ls. The scattered light Ls is scattered light generated by irradiating the floating particle 50 of the measurement target with the laser beam L1 emitted from the laser light emitting element 11. The backscattered light Lbs is return light which travels toward the laser light irradiator 10.

The back-monitor-value holder 33 extracts the DC-component signal Sdc separated by the DC/AC separator 32 at a predetermined designated time and then temporarily holds it. The back-monitor-value holder 33 may update the held value at every predetermined designated time. The held value may be a mean value of multiple extracted values, and so on. The back-monitor-value holder 33 supplies the held DC-component value Dp, as a signal S33, to the light emitting element controller 40 and the first identification unit 34.

Figure 2:
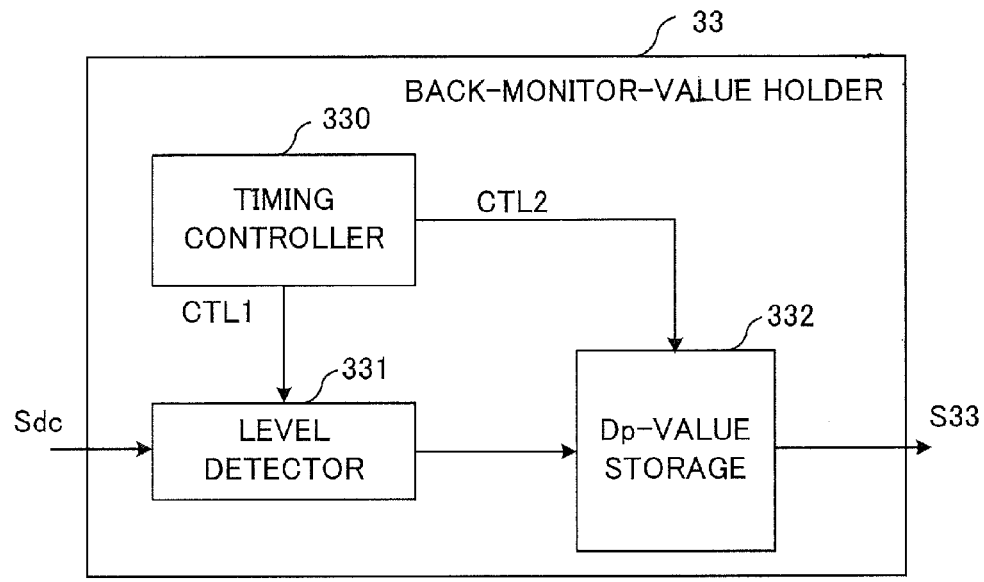
FIG. 2 is a block diagram showing an internal configuration of a back-monitor-value holder.
Figure 3:
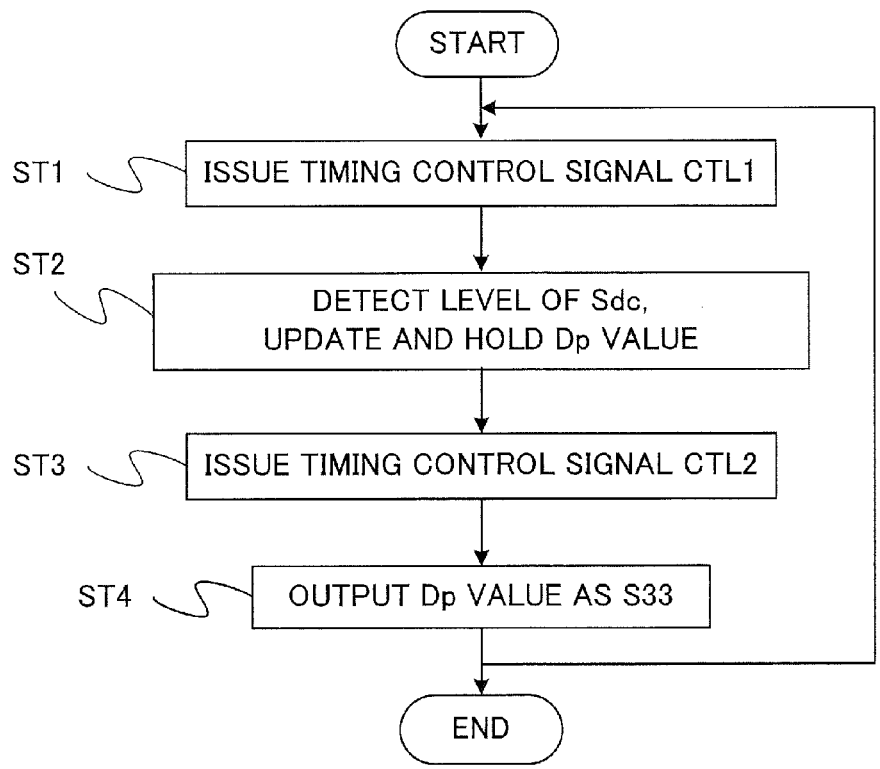
FIG. 3 is a flowchart showing internal processing of the back-monitor-value holder.

FIG. 2 is a block diagram showing an internal configuration of the back-monitor-value holder 33. FIG. 3 is a flowchart showing internal processing of the back-monitor-value holder 33. A timing controller 330 outputs a control signal CTL1 (step ST1). On the basis of this, a level detector 331 detects a level value of the DC-component signal Sdc of the detection signal S31. Then, the level detector 331 causes a Dp-value storage 332 to update and hold the level value of the signal Sdc, as a level value Dp (step ST2). The timing controller 330 outputs a control signal CTL2 (step ST3). On the basis of this, the Dp-value storage 332 outputs the level value Dp held in the Dp-value storage 332 at that time point, as a signal S33 (step ST4). The back-monitor-value holder 33 is capable of repeating the process of step ST1 to step ST4 at times set in the timing controller 330.

The light emitting element controller 40 controls a light emission amount of the irradiation laser beam L1 on the basis of the value Dp of the signal S33 generated by the back-monitor-value holder 33. For example, the light emitting element controller 40 reduces fluctuation in the light emission amount of the irradiation laser beam L1 caused by a gradual change of light emission efficiency due to a change of ambient temperature and so on. For this purpose, the light emitting element controller 40 controls a drive current value so as to keep it a value obtained by multiplying the value Dp by a certain constant. The drive current value is a current value to make the laser light irradiator 10 emit light. The control of the drive current value by the light emitting element controller 40 is carried out at intervals of time from an update time point in which the value Dp is updated to a next update time point. Such feedback control makes it possible to stabilize the light emission amount of the irradiation laser beam L1.

The first identification unit 34 receives the value Dp, DC-component signal Sdc and AC-component signal Sac. Then, the first identification unit 34 detects at least one of size of the floating particle 50 and density of the floating particles 50 on the basis of these values. The value Dp is the value of the DC component held in the back-monitor-value holder 33. The DC-component signal Sdc is the DC component separated by the DC/AC separator 32. The AC-component signal Sac is the AC component separated by the DC/AC separator 32. The first identification unit 34 calculates the size of the floating particle 50 or the density of the floating particles 50 on the basis of these input values. The size of the floating particle 50 can be identified on the basis of a degree of a change of the output signal by the back-monitor-use light receiving element 12. The density of the floating particles 50 can be identified on the basis of a change of the detection signal Sdc from the value Dp (held value) indicating the light emission amount which is held at a certain time.

The second identification unit 35 receives the voltage signal S24 which corresponds to the detection signal S21 generated by the scattered light detection element 21. The second identification unit 35 identifies a shape of the floating particle 50 on the basis of the signal S24. In other words, the second identification unit 35 identifies the shape of the floating particle 50 from the polarization component of the scattered light Ls which has passed through the polarizing filter 22.

The third identification unit 36 identifies the type of the floating particle 50 on the basis of information S34 and information S35. Then, the third identification unit 36 outputs information S36 which is the result of the identification. The information S34 is information on at least one of the size of the floating particle 50 and the density of the floating particles 50 obtained from the first identification unit 34. The information S35 is information on the shape of the floating particle 50 obtained from the second identification unit 35.

Figure 4:
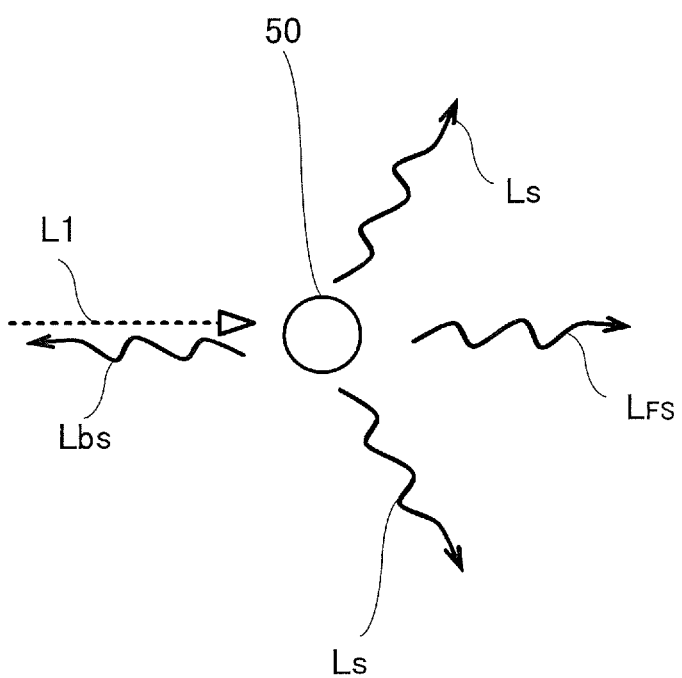
FIG. 4 is a diagram schematically showing major scattered light generated when a floating particle is irradiated with a laser beam.

FIG. 4 is a diagram schematically showing major scattered light generated when the floating particle 50 is irradiated with irradiation light (e.g. the irradiation laser beam L1). The irradiation laser beam L1 is light emitted from the laser light emitting element 11. The scattered light Ls is light scattered when the irradiation laser beam L1 strikes the floating particle 50. The scattered light Lbs is light travelling toward the laser light emitting element 11. That is, the scattered light Lbs is light travelling backward. Scattered light Lfs is light travelling forward. The scattered light Ls is light travelling toward the scattered light detection element 21. Here, an explanation for general scattering will be given. Irradiation of irradiation light (it is not limited to a laser beam) having a wavelength the length of which is comparatively close to the size of the floating particle 50 generally generates the scattered light. The scattered light Ls can be broadly separated into the forward-scattered light Lfs generated in a propagation direction of the irradiation laser beam L1 and scattered light generated in other directions. According to the shape and size of the floating particle 50, a ratio of the intensity of the scattered light changes. For example, the larger the size (diameter) of the floating particle 50 is, the greater the intensity of the scattered light is. According to the shape and size of the floating particle 50, a distribution (distribution of scattering intensity) of the scattered light toward each direction from the floating particle 50 changes. The intensity of the scattered light Ls is extremely small in comparison with the intensity of the irradiation laser beam L1. Further, as a part of the scattered light Ls, there is also the backward scattered light Lbs travelling in the direction opposite to the travel direction of the incident light (irradiation laser beam L1).

In the floating particle detection device 1 according to the first embodiment, the scattered light receiver 20 is disposed on a side or in front of the irradiation laser beam L1. The scattered light receiver 20 receives sideward-scattered light or forward-scattered light generated when the floating particle 50 is irradiated with the irradiation laser beam L1.

The polarizing filter 22 transmits only a polarization component orthogonal to light which propagates toward the light receiver side while its polarization direction is maintained and only the direction is changed even after the irradiation laser beam L1 is scattered. That is, the polarizing filter 22 transmits only a polarization component which is orthogonal to the irradiation laser beam L1 after the scattering. The irradiation laser beam L1 after the scattering is light propagating toward the light receiver (the scattered light detection element 21), while its polarization direction is maintained and only the direction is changed.

The floating particle detection device 1 according to the first embodiment uses polarization properties of a laser beam for identifying the shape of the floating particle 50. Pollen is floating particles having comparatively smooth surfaces and a shape like a spherical shape. Such particles are called 'spherical-shaped particles', since they have the shape like a spherical shape. On the other hand, as to dead bodies of mites, house dust, dust and the like, a lot of floating particles with rough surfaces and asymmetrical shapes is included. Such particles are called 'irregular-shaped particles', since their shapes are different from the spherical shape. When such an irregular-shaped particle is irradiated with light of linear polarization, a polarization component of the light of linear polarization is changed due to scattering. That is, light of a polarization component which is orthogonal to a polarization component of the irradiated light is generated as scattered light. Such a phenomenon is generally called depolarization. Because of the phenomenon of depolarization, when an irregular-shaped particle is irradiated with the irradiation laser beam L1, the scattered light includes light of a polarization component which is orthogonal to a linear polarization component of the irradiation laser beam L1. In the first embodiment, a polarization component in a polarization direction which differs from the polarization direction of the irradiation laser beam L1 is detected, in the scattered light Ls, to use it for identification of the shape.

How to identify the shape of the floating particle by the second identification unit 35 will be described below. In the first embodiment, the polarizing filter 22 is set so as to transmit only a polarization component having the polarization direction which is orthogonal to the polarization direction of the irradiation laser beam L1. In a case where the floating particle 50 is a spherical-shaped particle, a polarization direction of the scattered light Ls is the same as the polarization direction of the irradiation laser beam L1. For this reason, the scattered light Ls cannot pass through the polarizing filter 22. The scattered light detection element 21 outputs 0 (zero). On the other hand, in a case where the floating particle 50 is an irregular-shaped particle, the scattered light Ls includes a polarization component having a polarization direction which is different from the polarization direction of the irradiation laser beam L1. For this reason, the scattered light detection element 21 outputs a detection value corresponding to the degree of shape irregularity of the floating particle 50. The 'degree of shape irregularity' means the degree of how much it deviates from a spherical shape. The degree of shape irregularity (shape irregularity degree) can be indicated, when a particle is approximated to an ellipsoidal sphere, as a ratio between the length of a long axis and the length of a short axis of the ellipsoidal sphere. The degree of shape irregularity can also be indicated, when a particle is approximated to an ellipsoidal sphere, as a difference value between the length of a long axis and the length of a short axis of the ellipsoidal sphere, and so on.

FIG. 5 is a diagram showing polarization directions or polarization components on a plane perpendicular to an optical axis. In FIG. 5, parts A and B show the polarization directions of the irradiation laser beam with which irregular-shaped and spherical-shaped floating particles are irradiated in the floating particle detection device according to the first embodiment, with double-headed arrows on the plane perpendicular to the optical axis; parts C and D show polarization directions of scattered light generated when the irregular-shaped and spherical-shaped floating particles are irradiated with the irradiation laser beam, with double-headed arrows on the plane perpendicular to the optical axis; parts E and F show polarization components of the scattered light in the direction which is orthogonal to the polarization direction of the irradiation laser beam; and parts G and H show polarization components of the scattered light in the same direction as the polarization direction of the irradiation laser beam. In parts A to H of FIG. 5, horizontal axes are x axes. In parts A to H of FIG. 5, vertical axes are y axes. Z axes which are perpendicular to x-y planes are respective travel directions of the irradiation laser beam L1 and the scattered light. The polarization direction of the irradiation laser beam L1 is a y-axis direction. The x axis is a direction which is orthogonal to the polarization direction (y-axis direction). Part A of FIG. 5 is a diagram showing the polarization direction of the irradiation laser beam L1 with which the irregular-shaped floating particle is irradiated, with the double-headed arrow on the plane perpendicular to the optical axis, in the floating particle detection device 1 according to the first embodiment. Part B of FIG. 5 is a diagram showing the polarization direction of the irradiation laser beam L1 with which the spherical-shaped floating particle is irradiated, with the double-headed arrow on the plane perpendicular to the optical axis, in the floating particle detection device 1 according to the first embodiment. Part C of FIG. 5 is a diagram showing the polarization direction of the scattered light Ls generated when the irregular-shaped floating particle is irradiated with the irradiation laser beam L1, with the double-headed arrow on the plane perpendicular to the optical axis. Part D of FIG. 5 is a diagram showing the polarization direction of the scattered light Ls generated when the spherical-shaped floating particle is irradiated with the irradiation laser beam L1, with the double-headed arrow on the plane perpendicular to the optical axis. Part E of FIG. 5 is a diagram showing the polarization component of the scattered light Ls from the irregular-shaped floating particle in a direction which is orthogonal to the polarization direction of the irradiation laser beam L1 (x-axis direction). Part F of FIG. 5 is a diagram showing the polarization component of the scattered light Ls from the spherical-shaped floating particle in the direction which is orthogonal to the polarization direction of the irradiation laser beam L1 (x-axis direction). Part G of FIG. 5 is a diagram showing the polarization component of the scattered light Ls from the irregular-shaped floating particle in the same direction as the polarization direction of the irradiation laser beam L1 (y-axis direction). Part H of FIG. 5 is a diagram showing the polarization component of the scattered light Ls from the spherical-shaped floating particle in the same direction as the polarization direction of the irradiation laser beam L1 (y-axis direction). As in parts A and B of FIG. 5, the irradiation laser beam L1 which is irradiation light is light of linear polarization having amplitude in the up-down direction of the diagram (y-axis direction).

As regards the scattered light Ls shown in part C of FIG. 5, the polarization direction is turned. The polarization direction of the scattered light Ls shown in part C of FIG. 5 is turned clockwise (the polarization direction in part C of FIG. 5 is an example and it may be counterclockwise), with respect to the polarization direction of the irradiation laser beam L1 shown in part A of FIG. 5. If the floating particle 50 is an irregular-shaped particle, due to the phenomenon of depolarization, the polarization of the scattered light Ls is turned as shown in part C of FIG. 5, for example. The scattered light Ls shown in part D of FIG. 5 maintains the polarization direction. The polarization direction of the scattered light Ls shown in part D of FIG. 5 is the same as the polarization direction of the irradiation laser beam L1 shown in part B of FIG. 5. That is, the polarization direction of the scattered light Ls shown in part D of FIG. 5 is parallel to the y axis. If the floating particle 50 is a spherical-shaped particle, as shown in part D of FIG. 5, the polarization is not turned and the polarization direction of the scattered light Ls is the same as the polarization direction of the irradiation laser beam L1.

Parts E and G of FIG. 5 show a state where the scattered light Ls in part C of FIG. 5 is separated into the component of the polarization direction of the irradiation laser beam L1 in part A of FIG. 5 and the component of the direction which is orthogonal thereto. That is, parts E and G of FIG. 5 show the state where the scattered light Ls in part C of FIG. 5 is separated into the y-axis-direction component and the x-axis-direction component. Part E of FIG. 5 shows a state where the scattered light Ls in part C of FIG. 5 is separated into the x-axis-direction component. Part E of FIG. 5 shows the component of the scattered light Ls in the same direction as the direction orthogonal to the polarization direction of the irradiation laser beam L1. The polarization component which is in orthogonal relationship to the irradiation laser beam L1 is the polarization component shown in part E of FIG. 5. The polarization component of the scattered light Ls shown in part E of FIG. 5 exists. The part G of FIG. 5 shows a state where the scattered light Ls in part C of FIG. 5 is separated into the y-axis-direction component. Part G of FIG. 5 shows the component of the scattered light Ls in the same direction as the polarization direction of the irradiation laser beam L1. These diagrams (parts E and G of FIG. 5) show an example, and turn directions or turn angles of the polarization are not specially limited. When the scattered light Ls enters the scattered light receiver 20, the polarizing filter 22 is set so as to transmit only the polarization component which is in orthogonal relationship to the polarization component of the irradiation laser beam L1 which is irradiation light. For this reason, if the floating particle 50 is an irregular-shaped (i.e., nonspherical-shaped) particle, as shown in part C of FIG. 5, a part of the polarization component of the scattered light Ls becomes a polarization component having an oblique polarization direction in part C of FIG. 5. Accordingly, of the scattered light Ls shown in part C of FIG. 5, only the polarization component which is in orthogonal relationship to the irradiation laser beam L1 which is irradiation light is received by the scattered light detection element 21.

On the other hand, if the shape of the floating particle 50 is close to a spherical shape, the phenomenon of depolarization hardly occurs. For example, as shown in part D of FIG. 5, a polarization state in which the scattered light Ls has the same polarization direction as the polarization direction (y-axis direction) of the irradiation laser beam L1 is maintained. As shown in parts F and H of FIG. 5, they are diagrams showing a state where the scattered light in part D of FIG. 5 is separated into the respective components. That is, parts F and H of FIG. 5 show the state where the scattered light Ls in part D of FIG. 5 is separated into the y-axis-direction component and the x-axis-direction component. Part F of FIG. 5 shows a state where the scattered light Ls in part D of FIG. 5 is separated into the x-axis-direction component. Part F of FIG. 5 shows the component of the scattered light Ls in the same direction as the direction which is orthogonal to the polarization direction of the irradiation laser beam L1. Part H of FIG. 5 shows a state where the scattered light Ls in part D of FIG. 5 is separated into the y-axis-direction component. Part H of FIG. 5 shows the component of the scattered light Ls in the same direction as the polarization direction of the irradiation laser beam L1. The polarization component of the scattered light Ls shown in part F of FIG. 5 is substantially zero. As shown in part F of FIG. 5, the polarization component which is orthogonal to the polarization direction (y-axis direction) of the irradiation laser beam L1 hardly exists. Since the scattered light Ls is hardly transmitted through the polarizing filter 22, a value Sp of the output signal S21 from the scattered light detection element 21 is substantially 0 (zero).

Thus, it is possible to identify whether the shape of the floating particle 50 is irregular or spherical from the value Sp of the output signal S24. Alternatively, a judgment whether or not the value Sp is at or below a predetermined level makes it possible to identify whether the shape of the floating particle 50 is irregular or spherical.

FIG. 6(a) is a diagram schematically showing an example of a detection waveform when the scattered light detection element 21 of the scattered light receiver 20 in the floating particle detection device 1 according to the first embodiment detects scattered light from an irregular-shaped particle. FIG. 6(b) is a diagram schematically showing an example of a detection waveform when the scattered light detection element 21 of the scattered light receiver 20 in the floating particle detection device 1 according to the first embodiment detects scattered light from a spherical particle. In FIG. 6(a) and FIG. 6(b), horizontal axes represent time and vertical axes represent signal values (signal levels). In FIG. 6(a) and FIG. 6(b), small fluctuations in the waveforms in the vicinity of zero level represent noise. In addition, in FIG. 6(a) and FIG. 6(b), no small fluctuations (noise) are shown in large waveform peaks for convenience, but in actuality noise waveforms (small fluctuations) are also superimposed on the large waveform peaks.

A waveform of the signal S24 from the scattered light detection element 21 is as in FIG. 6(a) or FIG. 6(b), for example. The waveform in FIG. 6(a) has two waveform peaks larger than a threshold value THp. The two waveform peaks are waveform peaks due to the scattered light Ls. A peak value P of one of the waveform peaks is a value Pa1. A peak value P of the other waveform peak is a value Pa2. Since the value Pa1 of the peak value P is larger than the threshold value THp, it is judged that the floating particle 50 is an irregular-shaped particle. Since the value Pa2 of the peak value P is larger than the threshold value THp, it is judged that the floating particle 50 is an irregular-shaped particle. In FIG. 6(a), small wavy lines shown in the vicinity of where the signal level (the vertical axis) is substantially zero represent noise. That is, as shown in FIG. 6(a), in a case where the shape of the floating particle 50 is the irregular shape, a large waveform peak such as the peak values P=Pa1 and P=Pa2 is detected. On the other hand, the waveform in FIG. 6(b) has two waveform peaks which are smaller than the threshold value THp. The two waveform peaks are waveform peaks due to the sideward scattered light Ls. A peak value P of one of the waveform peaks is a value Ps1. A peak value P of the other waveform peak is a value Ps2. Since the value Ps1 of the peak value P is not larger than the threshold value THp, it is judges that the floating particle 50 is a spherical-shaped particle. Since the value Ps2 of the peak value P is not larger than the threshold value THp, it is judged that the floating particle 50 is a spherical-shaped particle. In FIG. 6(b), small wavy lines shown in the vicinity of where the signal level (vertical axis) is substantially zero represent noise. As shown in FIG. 6(b), in a case where the floating particle 50 is spherical in shape, small waveform peaks such as the peak values P=Ps1 and P=Ps2 are detected or in a case where the floating particle 50 is spherical in shape, no waveform peak is detected. In this case, by using the predetermined threshold value THp, when a peak value P of a waveform peak exceeds the threshold value THp, it is possible to identify that the floating particle 50 is irregular in shape. When a peak value P of a waveform peak is not larger than the threshold value THp, it is possible to identify that the floating particle 50 is spherical in shape. The threshold value THp is set to be a value that is larger than a noise level other than the detection signal and sufficiently smaller than a peak value P of the value Sp of the signal S24 of the irregular-shaped particle.

In addition, a degree of depolarization varies depending on the shape irregularity degree of the irregular-shaped particle. In general, the larger the shape irregularity degree of an irregular-shaped particle is, the larger the degree of depolarization is. The 'degree of shape irregularity' means the degree of how much it deviates from a sphere. From this, depending on it, the size of the component (polarization component) in the polarization direction (x-axis direction) which is orthogonal to the polarization direction of the irradiation laser beam L1 (y-axis direction varies. Thus, depending on the degree of shape irregularity of the irregular-shaped particle, the peak value P of the value Sp (signal level) of the signal S24 corresponding to the scattered light Ls from the scattered light detection element 21 varies. Thus, another threshold value which is used for identifying the degree of shape irregularity of the irregular-shaped particle is set in advance, and then the degree of shape irregularity is determined from the size relationship between the threshold value and a peak value P of the value Sp of the signal S24. This can be also used, for identifying the type of the floating particle, as the result information S35 on identification of the shape of the floating particle. The result information S35 is output from the second identification unit 35.

In the configuration described above, the polarizing filter 22 is set so as to transmit only the polarization component in the polarization direction (x-axis direction) which is orthogonal to the polarization direction (y-axis direction) of the irradiation laser beam L1. However, the configuration that the polarizing filter 22 is set so as to transmit only the polarization component in the same polarization direction (y-axis direction) as the polarization direction (y-axis direction) of the irradiation laser beam L1 is also possible. In this case, reference data obtained by measuring in advance a relationship between the particle shapes and the signal S24 is stored in a memory or the like. Alternatively, reference data obtained by calculating in advance the relationship between the particle shapes and the signal S24 is stored in a memory or the like. Then, by using the value Sp of the signal S24 and the reference data, it is possible to identify whether it is an irregular-shaped particle or a spherical-shaped particle.

However, in a case where the polarizing filter is set so as to transmit only the polarization component in the polarization direction (x-axis direction) which is orthogonal to the polarization direction (y-axis direction) of the irradiation laser beam L1, an output signal from the scattered light detection element 21 appears only when it is an irregular-shaped particle. Thus, there is an advantage that identifying whether or not the output signal S21 from the scattered light detection element 21 is present makes it possible to identify whether the floating particle is an irregular-shaped or a spherical-shaped particle. There is another advantage that identification of the shape of the floating particle can be also easily performed.

At the time of determining the degree of shape irregularity, a peak value P of the value Sp (signal level) of the signal S24 corresponding to the scattered light from the scattered light detection element 21 may be one which is normalized by using a level value Ak (k is an integer) of the AC-component signal Sac corresponding to the backscattered light Lbs of the scattered light Ls (i.e., P/Ak). The normalized peak value P of the value Sp (signal level) of the signal S24 will be hereinafter referred to as a 'normalized peak value'. As to the sideward scattered light (scattered light Ls) and backscattered light Lbs, the light amount also varies due to various factors such as the size of the floating particle 50 and light absorption characteristics of the material of the particle. These factors cause a change in the light amount of the scattered light itself to be included in the value P of the signal Sp.

Figure 7:
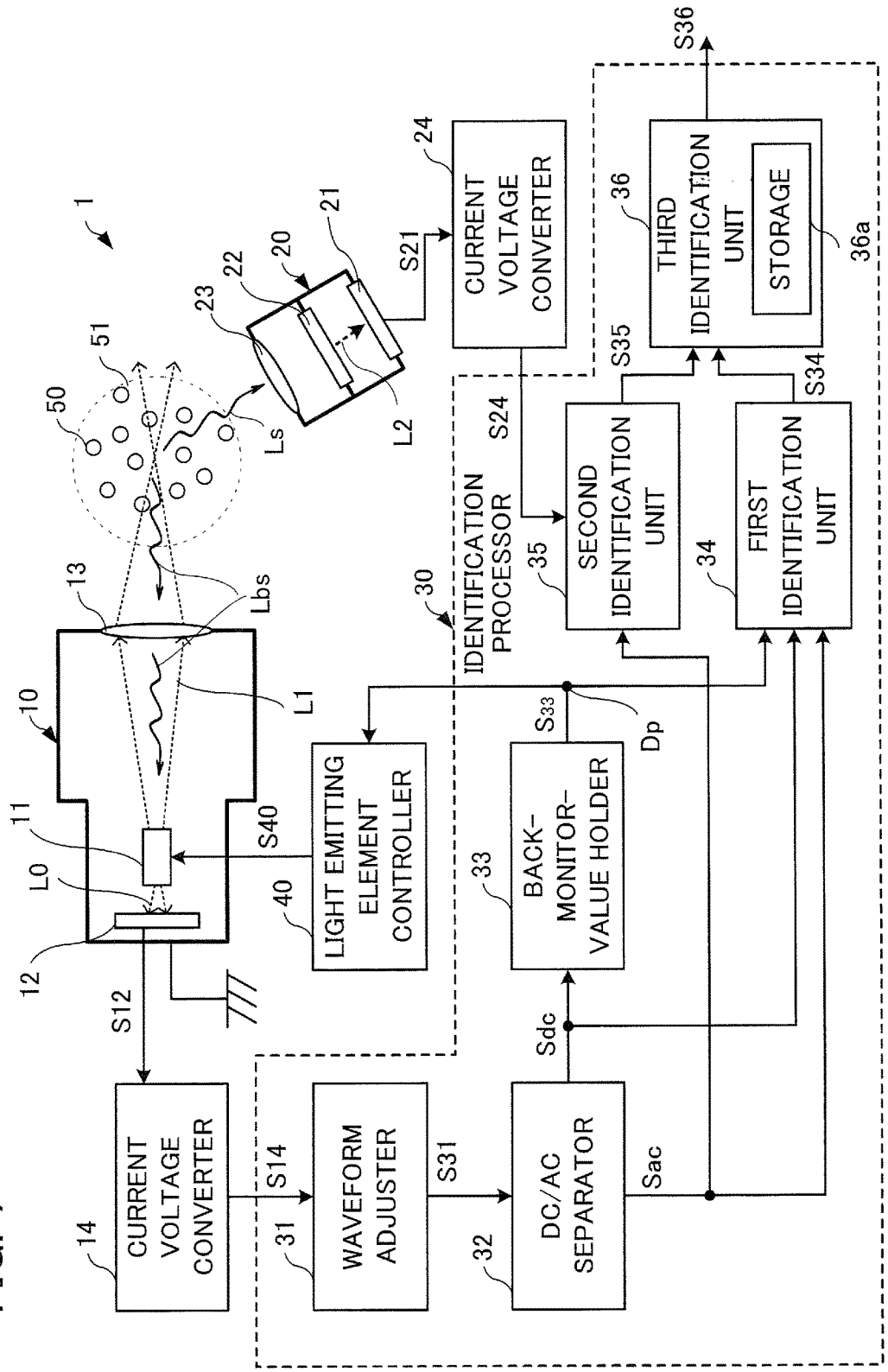
FIG. 7 is a diagram schematically showing a configuration of the floating particle detection device according to the first embodiment.

By carrying out this normalization, it is possible to cancel a change in the peak value P of the value Sp (signal level) of the signal S24 due to a change in the light amount of the scattered light itself. It is also possible to reduce an error in identification of the degree of shape irregularity by the size determination of the peak value P of the value Sp (signal level) of the signal S24 with reference to the threshold value THp. FIG. 7 is a diagram schematically showing a configuration of the floating particle detection device 1 according to the first embodiment when the normalized peak value P/Ak is used. The configuration for inputting the AC component Sac of the signal S31 output from the DC/AC separator 32 to the second identification unit 35 is additionally added, in comparison to the configuration of the floating particle detection device 1 shown in FIG. 1.

Figure 8:
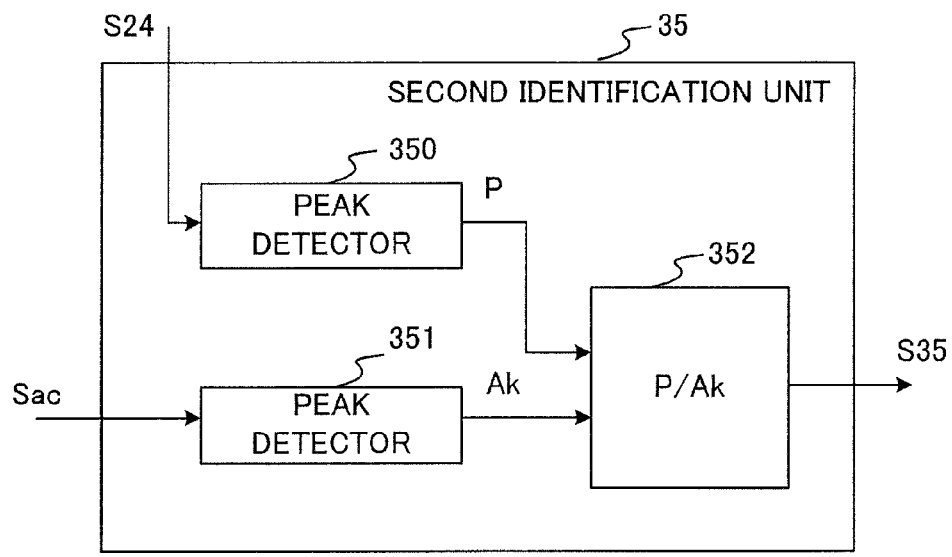
FIG. 8 is a block diagram showing internal processing of a second identification unit in a case where a normalized peak value is applied.
Figure 9:
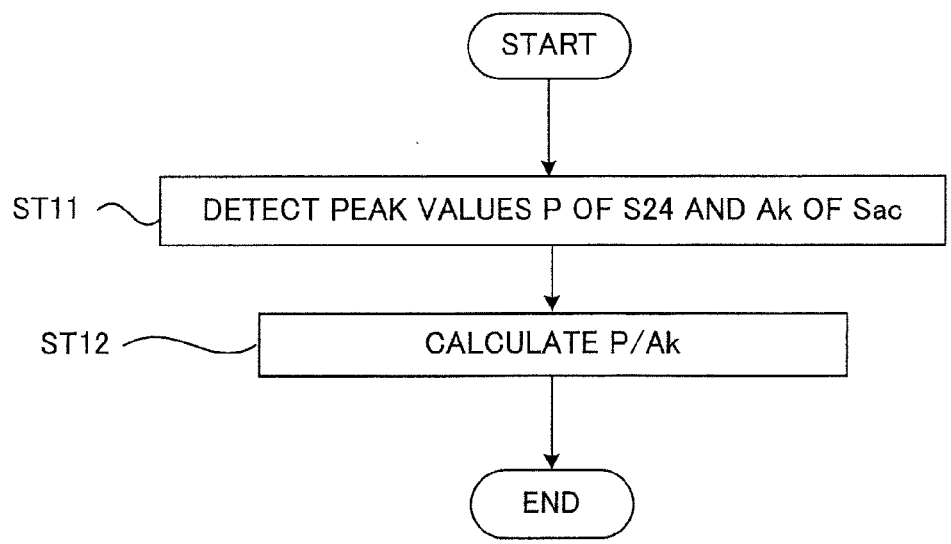
FIG. 9 is a flowchart showing a flow of the internal processing of the second identification unit.

FIG. 8 is a block diagram showing internal processing of the second identification unit 35 in a case where the normalized peak value is applied. FIG. 9 is a flowchart showing a flow of the internal processing of the second identification unit 35. A peak detector 350 detects the peak value P of the value Sp of the signal S24. Then, a peak detector 351 detects the level value Ak which is a peak of the AC-component signal Sac of the detection signal S31 (step ST11). Then, a normalized-peak-value calculator 352 normalizes the peak value P by using the level value Ak. Then, the normalized-peak-value calculator 352 outputs a normalized signal S35 (step ST12).

Figure 10A:
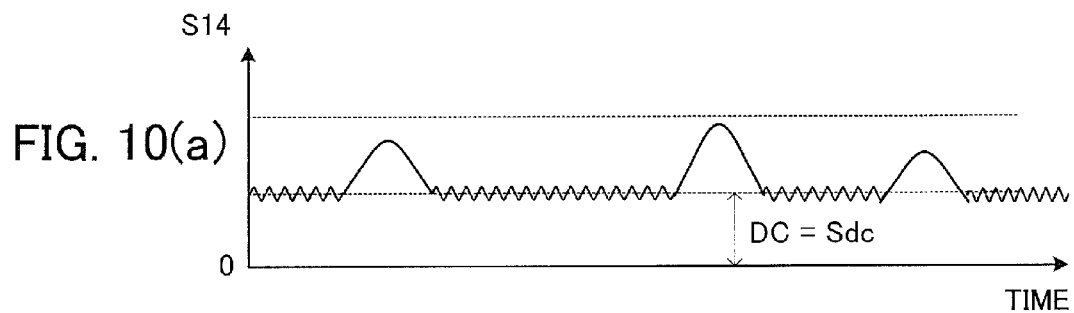
FIG. 10(a) is a diagram schematically showing an example of a detection waveform which is detected by a back-monitor-use light receiving element and is input to a waveform adjuster in the floating particle detection device according to the first embodiment.

FIG. 10(a) is a diagram schematically showing an example of a detection waveform (voltage signal S14) which is detected by the back-monitor-use light receiving element 12 and is input to the waveform adjuster 31 in the floating particle detection device 1 according to the first embodiment. The waveform in FIG. 10(a) has three waveform peaks which are smaller than a threshold value THa. In FIG.

10(a), the threshold value THa is shown so as to be added to a signal level DC. That is, the threshold value THa is a value based on the signal level DC. The three waveform peaks are waveform peaks due to the backscattered light Lbs. In FIG. 10(a), small wavy lines shown in a position of the signal level DC from the signal level (vertical axis) zero represent noise. The signal level DC is a value of the DC-component signal Sdc of the detection signal S31. That is, it is a DC component due to the back-monitor-use laser beam L0.

Figure 10B:
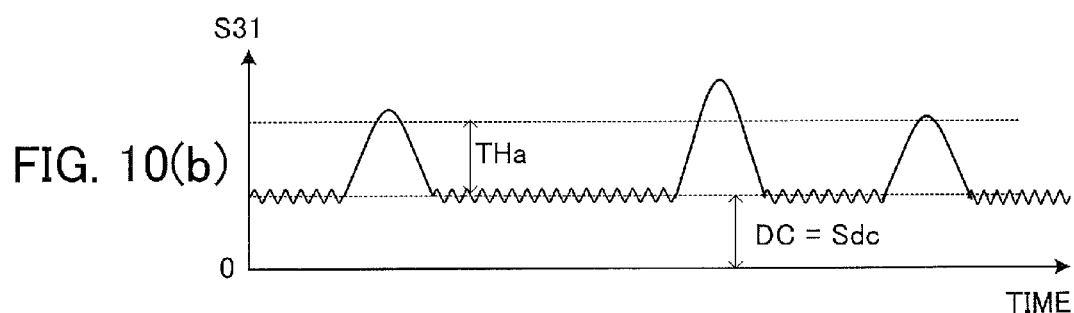
FIG. 10(b) is a diagram schematically showing an example of the detection waveform adjusted by the waveform adjuster in the floating particle detection device according to the first embodiment.

FIG. 10(b) is a diagram schematically showing an example of the detection waveform (the first detection signal S31) adjusted by the waveform adjuster 31 in the floating particle detection device 1 according to the first embodiment. The waveform in FIG. 10(b) has three waveform peaks which are larger than the threshold value THa. In FIG. 10(b), the threshold value THa is shown so as to be added to the signal level DC. That is, the threshold value THa is a value based on the signal level DC. The three waveform peaks are waveform peaks due to the backscattered light Lbs. In FIG. 10(b), small wavy lines shown in a position of the signal level DC from the signal level (vertical axis) zero represent noise. The signal level DC is a value of the DC-component signal Sdc of the detection signal S31. That is, it is a DC component due to the back-monitor-use laser beam L0.

Figure 10C:
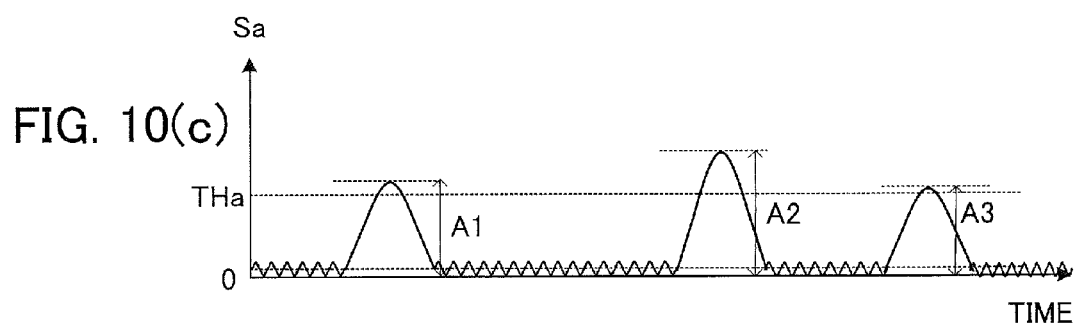
FIG. 10(c) and FIG. 10(d) are diagrams schematically showing a waveform of an alternating-current component and a waveform of a direct-current component generated by a direct-current/alternating-current separator in the floating particle detection device according to the first embodiment.

FIG. 10(c) is a diagram schematically showing a waveform of the AC-component signal Sac generated by the DC/AC separator 32 in the floating particle detection device 1 according to the first embodiment. The waveform in FIG. 10(c) has three waveform peaks which are larger than the threshold value THa. In FIG. 10(c), the threshold value THa is a value based on a value the signal level of which is zero. The three waveform peaks are waveform peaks due to the backscattered light Lbs. In FIG. 10(c), small wavy lines shown in a position where the signal level (vertical axis) is zero represent noise. The amplitude An (n=1, 2, 3) of the three waveform peaks represents the particle size of the floating particle 50. The number of waveform peaks indicates the number of the floating particles 50. The frequency of waveform peaks indicates the density of the floating particles 50.

Figure 10D:
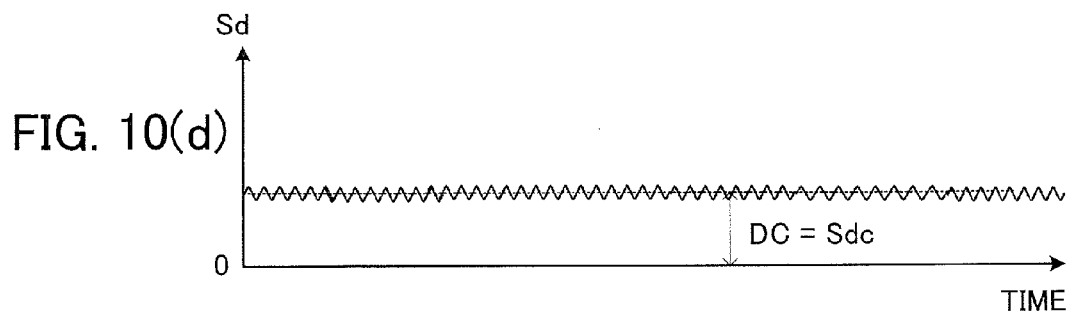

FIG. 10(d) is a diagram schematically showing a waveform of the DC-component signal Sdc generated by the DC/AC separator 32 in the floating particle detection device 1 according to the first embodiment. In FIG. 10(d), small wavy lines shown in a position of the signal level DC from the signal level (vertical axis) zero represent noise. The signal level DC is a value of the DC-component signal Sdc of the detection signal S31.

In FIG. 10(a) to FIG. 10(d), horizontal axes represent time and vertical axes represent signal values (signal levels). The small fluctuations in the waveforms of the DC components in FIG. 10(a) to FIG. 10(d) represent noise. No small fluctuations (noise) are shown on the large waveform peaks (large fluctuations) in FIG. 10(a) to FIG. 10(c) for convenience, but noise waveforms (small fluctuations) also overlap the large waveform peaks in actuality.

The backscattered light Lbs travelling backward among the scattered light Ls caused by the floating particle 50 is transmitted through the condenser lens 13, and travels toward the back-monitor-use light receiving element 12. In other words, the scattered light Ls propagates from each of the plurality of the floating particles 50 at various angles (in various directions). Accordingly, a part of the scattered light Ls becomes the backscattered light Lbs which travels directly toward the back-monitor-use light receiving element 12. The backscattered light Lbs enters the laser light irradiator 10. This makes it possible to detect the scattered light Ls from the output value Sdc of the current signal S12 of the back-monitor-use light receiving element 12.

As an alternative method, the scattered light Ls does not directly enter the back-monitor-use light receiving element 12, but enters the front-side edge surface of the laser light emitting element 11 as the return light. Due to this, the amount of light emission of the laser light emitting element 11 from the back-side edge surface toward the back-monitor-use light receiving element 12 also varies according to it. This is also referred to as fluctuations of the back-monitor-use laser beam L0. By using this phenomenon, it is possible to detect the scattered light Ls from the output value Sdc of the back-monitor-use light receiving element 12 (the DC component of the detection signal S31). In general, if a part of the emitted light L1 is reflected and enters through the front-side edge surface of the laser light emitting element 11, light intensity distribution in the semiconductor laser chip is disturbed by this and a laser oscillation state also varies. Following this, the amount of light emission of the laser light emitting element 11 from the back-side edge surface on the side of the back-monitor-use light receiving element 12 also varies. In the first embodiment, it is also possible to use such fluctuations of the back-monitor-use laser beam L0.

In the first embodiment, the scattered light Ls from the floating particle 50 is self-detected by the back-monitor-use light receiving element 12 on the light source side, as the return light toward the laser light emitting element 11. The laser light emitting element 11 is a light source for irradiation. Thus, the floating particle detection device 1 detects the presence of the floating particle 50 or detects the size of the floating particle 50. This makes it unnecessary to include one of two detection optical systems for the scattered light Ls which were conventionally needed on the receiver side. Thus, in the first embodiment, it is possible for the floating particle detection device 1 to identify the type of the floating particle 50, by providing only the scattered light receiver 20. The scattered-light receiver 20 is a detection optical system for detecting one polarization component. Specific explanation will follow.

The first identification unit 34 identifies the size of the floating particle 50 by using the general fact that the larger the size (diameter) of the floating particle 50 is, the larger the intensity of the scattered light Ls is. The AC-component signal Sac of the detection signal S31 of the back-monitor-use light receiving element 12 varies according to scattering in the floating particle 50. That is, the first identification unit 34 identifies the size of the floating particle 50 from the size relationship between a signal change level of the AC signal Sac of the detection signal S31 and a preset threshold value for identification. The third identification unit 36 receives this as the result information S34 on identification of the floating-particle size and uses for identification of the type of the floating particle 50. Moreover, the first identification unit 34 counts the number of times of signal change of the AC-component signal Sac of the detection signal S31, for each size of the floating particle 50. This allows the third identification unit 36 to calculate a quantity of the floating particles 50 as the number of the floating particles 50 or the number of the floating particles 50 in an air volume.

By referring to FIG. 10(a) to FIG. 10(d), a specific explanation will be given. In the detection signal S14 of the back-monitor-use light receiving element 12, the fluctuations (waveform peaks) as in FIG. 10(a) appear whenever scattering occurs in the floating particle 50, because of a return of the scattered light Ls to the laser light irradiator 10, irrespective of the shape of the floating particle 50. That is, because of a return of the scattered light Ls to the laser light irradiator 10, in the detection signal S14, the fluctuations (waveform peaks) as in FIG. 10(*a*) appear whenever scattering occurs in the floating particle 50. The fluctuation (waveform peak) does not relate to the shape of the floating particle 50. In FIG. 10(*a*), three fluctuations (waveform peaks) appear. The maximum values of the waveform peaks in FIG. 10(*a*) are smaller than the threshold value THa. In FIG. 10(*a*) to FIG. 10(*d*), the fluctuation (waveform peak) is represented as a change of increase (a waveform peak on the plus side). However, in a case where it decreases due to the characteristics of the laser light emitting element 11, the polarity of the fluctuation change may be correspondingly the reverse (a waveform peak on the minus side) of that in the above case. The amplitude of the fluctuation (waveform peak) is generally small. For this reason, it is sometimes difficult to differentiate it from the amplitude level of another comparatively-high-frequency noise component. In that case, it is possible for the waveform adjuster 31 to form a waveform adjuster that emphasizes a signal component of the fluctuation (waveform peak), for example. By emphasizing the signal component of the fluctuation (waveform peak), the waveform can be corrected as in FIG. 10(*b*) (signal S31). The maximum values of the waveform peaks in FIG. 10(*b*) are larger than the threshold value THa. Next, the signal S31 is separated by the DC/AC separator 32 into the AC component (alternating-current component) signal Sac and the DC component (direct-current component) signal Sdc. The AC-component signal Sac of the signal S31 is shown in FIG. 10(*c*). In FIG. 10(*c*), whichever the shape of the floating particle 50 is, signal levels Ai and Ak of waveform peaks of the signal Sac are detected. Indexes i and k are integers not less than 1. In FIG. 10(*c*), a signal level A1, a signal level A2 and a signal level A3 are shown. These signal level Ai and signal level Ak are output levels corresponding to the diameter of the floating particle 50.

Thus, from the size relationship between the signal level Ai and signal level Ak and the preset threshold value THa for identification, the size of the floating particle 50 can be identified. By using the waveform in FIG. 10(*c*), the first identification unit 34 counts the number of times in which waveform peaks exceed the threshold value THa of the signal waveform, or measures the number of times per unit time (occurrence frequency), for each size of the floating particles 50. This makes it possible to calculate the quantity (density) of the floating particles 50 as the number of the floating particles 50 or the number of the floating particles in an air volume (in a unit volume).

Next, a method of identifying the density of the floating particles 50 at the first identification unit 34 will be explained. The DC-component signal Sdc of the signal S31 is shown in FIG. 10(*d*). The back-monitor-value holder 33 holds the value Dp (held value) of the signal Sdc shown in FIG. 10(*d*), at a certain time point. The certain time point of holding the value Dp is a time point of starting the floating particle detection device 1, for example. Alternatively, the time point of holding the value Dp is a time point of correcting, to necessary power, the irradiation light (irradiation laser beam L1) at a time of detection which should be set in the floating particle detection device 1, and so on. The time point of correcting to necessary power is a time point of power correction at a time of shipment, for example. There is no need to perform the power correction, unless the efficiency of light emission from the irradiator (the laser light irradiator 10) drastically decreases. That is, the power correction may be intermittently performed when necessary.

Until the next power correction processing, the value Dp of the detection signal Sdc before update is held in the back-monitor-value holder 33. In addition, if one detection process is defined as that from a start of the detection to identification of the type of the floating particle 50 in the end, it is desirable that a time interval between power corrections should be equal to or longer than a time required for at least one detection process. That is, the time interval between power corrections is one time in one detection, even if it is short.

The held value Dp and the value of the detection signal Sdc are input to the first identification unit 34. Then, the held value Dp and the value of the detection signal Sdc are used for identification of the density of the floating particles 50. In the above explanation, a case where the dispersion density of the floating particles 50 is comparatively low is presupposed. However, in a case where the dispersing floating particles 50 densely disperse like 'cigarette smoke' for example, a large number of the floating particles 50 are irradiated with the irradiation laser beam L1 at a time. Accordingly, a level of the return light (the backscattered light Lbs) changes in terms of time average. That is, it is detected not as a waveform corresponding to each of the floating particles 50 but as a change in the DC component (direct-current component) which is the signal Sdc.

Accordingly, from the held value Dp, a degree of the change of the value of the detection signal Sdc is monitored. Such monitoring makes it possible to identify that the floating particles 50 the dispersion density of which is high are detected. That is, when the value DC of the signal Sdc (a value of the DC component at the present time) shown in FIG. 10(*d*) is gradually changing with reference to the held value Dp with the lapse of time, the first identification unit 34 can identify that the floating particles 50 are those the dispersion density of which is high. Further, it is also possible for the first identification unit 34 to identify the dispersion density of the floating particles 50 according to the degree of the change.

Figure 12:
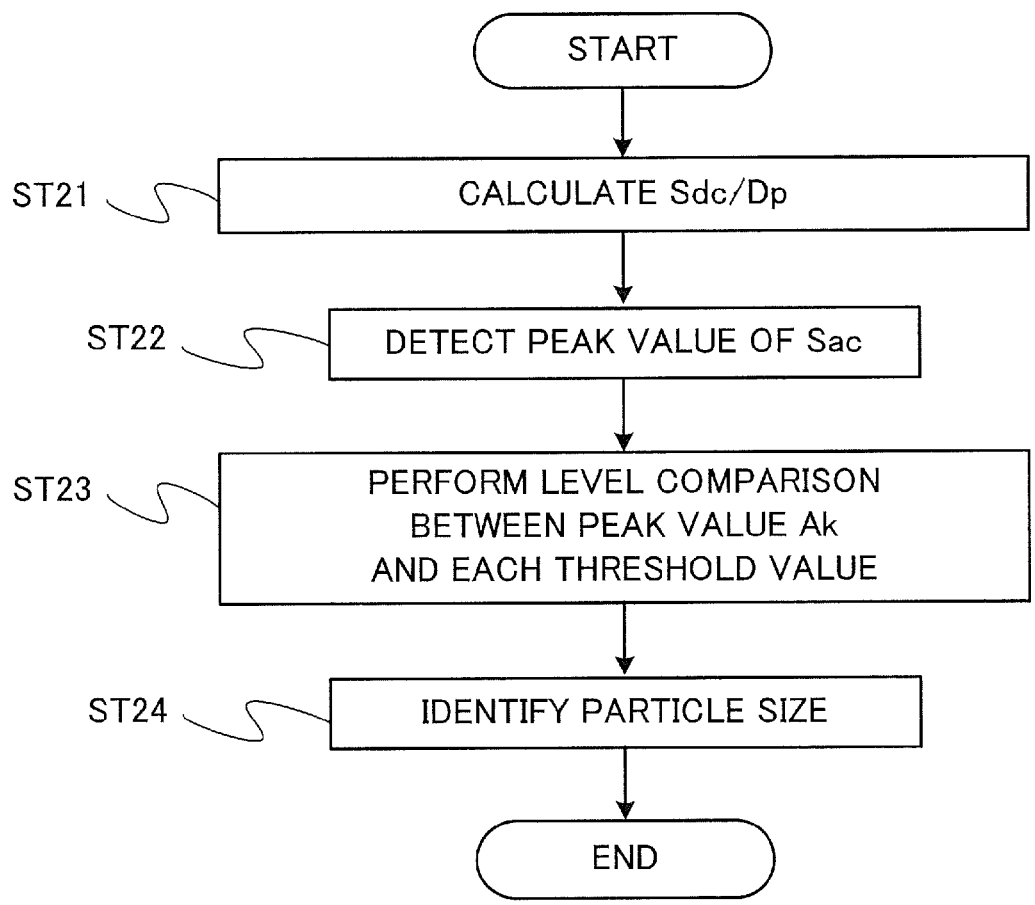
FIG. 12 is a flowchart showing a flow of the internal processing of the first identification unit.

FIG. 11 is a block diagram showing internal processing of the first identification unit 34. FIG. 12 is a flowchart showing a flow of the internal processing of the first identification unit 34.

The first identification unit 34 calculates a value Sdc/Dp obtained by normalizing the level value Dp with the value Sdc (step ST21). The level value Dp is a level value output from the back-monitor-value holder 33. The value Sdc is a value of the DC component output from the DC/AC separator 32. A peak detector 341 detects a peak value Ak of the AC-component value Sac output from the DC/AC separator 32 (step ST22). A level comparator 342 performs size comparison between the peak value Ak and each of the threshold values THa (step ST23). The threshold values THa are threshold values stored in a threshold value storage 343 in advance. The threshold values THa are, for example, THa25, THa100, THa250 and THa400 described below. A particle-size identification unit 344 identifies the particle size on the basis of the value Sdc/Dp and the result of the comparison by the level comparator 342 (step ST24). The result of the identification is output as a value S34 from the first identification unit 34. A detection number counter 345 counts the number of times of detection of waveform peaks by the peak detector 341. Then, a density calculator 346 receives from the peak detector 341 the value of the number of times of detection. The density calculator 346 calculates the number of times per unit time (occurrence frequency).

The third identification unit 36 identifies the type of the floating particle 50 on the basis of the result information S35 on the identification of the shape of the floating particle 50 by the second identification unit 35 and the result information S34 on the identification of the size of the floating particle 50 by the first identification unit 34. Then, the third identification unit 36 outputs the identification result S36. The third identification unit 36 includes a storage 36a.

FIG. 13 is a diagram schematically showing relationship between waveform peaks of the AC component generated by the DC/AC separator 32 in the floating particle detection device 1 according to the first embodiment and the threshold values THa25, THa100, THa250 and THa400. FIG. 14 is a diagram showing an example of identification of the types of the floating particles 50 according to combinations of the shapes of the floating particles 50 and sizes of the floating particles by the third identification unit 36 in the floating particle detection device 1 according to the first embodiment.

By referring to FIG. 13 and FIG. 14, a case where 'cigarette smoke', 'PM2.5', 'PM10', 'pollen' and 'house dust' are distinguished from each other will be explained.

FIG. 13 is a diagram schematically showing relationship between waveforms of the AC component (signal Sac) generated by the DC/AC separator 32 in the floating particle detection device 1 and the threshold values THa. In FIG. 13, five waveform peaks are shown. The first waveform peak represents PM2.5. An amplitude A11 of the first waveform peak is not larger than the threshold value THa25. That is, the amplitude A11 of the first waveform peak satisfies the relationship of A11≤THa25. The second waveform peak represents PM10. An amplitude A12 of the second waveform peak is larger than the threshold value THa25. The amplitude A12 of the second waveform peak is not larger than the threshold value THa100. That is, the amplitude A12 of the second waveform peak satisfies the relationship of THa25<A12≤THa100. The third waveform peak represents house dust or pollen. An amplitude A13 of the third waveform peak is larger than the threshold value THa100. The amplitude A13 of the third waveform peak is not larger than the threshold value THa250. That is, the amplitude A13 of the third waveform peak satisfies the relationship of THa100<A13≤THa250. The fourth waveform peak represents house dust or pollen. An amplitude A14 of the fourth waveform peak is larger than the threshold value THa250. The amplitude A14 of the fourth waveform peak is not larger than the threshold value THa400. That is, the amplitude A14 of the fourth waveform peak satisfies the relationship of THa250<A14≤THa400. The fifth waveform peak represents house dust. An amplitude A15 of the fifth waveform peak is larger than the threshold value THa400. That is, the amplitude A15 of the fifth waveform peak satisfies the relationship of THa400<A15. In addition, in FIG. 13, small wavy lines shown in a position where the signal level (vertical axis) is zero represent noise.

As to 'cigarette smoke', in general, its characteristic is that the floating particle diameter is not larger than 0.5 μm and the dispersion density is high. As to 'PM2.5', the floating particle 50 has the floating particle diameter which is not larger than 2.5 μm. As to 'PM10', the floating particle 50 has the floating particle diameter which is not larger than 10 μm. As to 'pollen', its characteristic is that the shape is comparatively close to the spherical shape. As to 'house dust' such as dead bodies of mites and dust, its characteristic is that the shape is unlikely to be the spherical shape and it is categorized as the irregular shape. These can be roughly sorted according to the diameter of the floating particle. However, 'pollen' and 'house dust' may be distributed in a similar size. For this reason, it is necessary to distinguish between 'pollen' and 'house dust' by using a criterion other than the size. In the criterion other than the size, it is necessary to distinguish, for example, by using their shapes.

FIG. 14 is a diagram showing an example of identification of the types of the floating particles 50 according to combinations of the shapes of the floating particles 50 and sizes of the floating particles 50 by the third identification unit in the floating particle detection device 1. In FIG. 14, the value Dp is a held value of the detection signal Sdc after the power correction. 'THc' is a threshold value for identifying 'cigarette smoke'. 'An' (n is an integer) is a value of the signal Sac. THa25, THa100, THa250 and THa400 are threshold values used for identifying that the diameter of the floating particle is not larger than 2.5 μm, not larger than 10 μm, not larger than 25 μm and not larger than 40 μm respectively. That is, THa25 is a threshold value used for identifying that the diameter of the floating particle is not larger than 2.5 μm. THa100 is a threshold value used for identifying that the diameter of the floating particle is not larger than 10 μm. THa250 is a threshold value used for identifying that the diameter of the floating particle is not larger than 25 μm. THa400 is a threshold value used for identifying that the diameter of the floating particle is not larger than 40 μm. The value P is a peak value of the value Sp of the signal S24. THp is a threshold value for identifying the shape irregularity degree with respect to the peak value P of the value Sp. If the peak value P is not larger than the threshold value THp, it is identified that the floating particle 50 is spherical in shape. On the other hand, if the peak value P is larger than the threshold value THp, it is identified that the floating particle 50 is irregular in shape. The threshold values THa25, THa100, THa250 and THa400 are set on the basis of one or both of the following two results (values). The first ones are results obtained by measuring in advance the relationship between the size of the floating particle 50 and the value An of the signal Sac (for example, the value A1 or value Ak). The second ones are estimation values based on the relationship between the size of the floating particle 50 and the value An of the signal Sac (for example, the value Ai or value Ak), which is obtained from the size of the floating particle 50 and a general physical theory regarding light scattering. The information in FIG. 14 is stored in advance in the storage 36a, for example.

As shown in FIG. 14, on the basis of the identification result information S34 and identification result information S35, the third identification unit 36 identifies whether the type of the floating particle 50 is 'cigarette smoke', 'pollen' or 'house dust'. The third identification unit 36 outputs the identification result information S36. The third identification unit 36 is a unit for identifying the type of the floating particle 50. The identification result information S34 is information on the result of the identification by the first identification unit 34. The identification result information S35 is information on the result of the identification by the second identification unit 35.

As described above, in the first embodiment, the floating particle detection device 1 is capable of identifying the type of the floating particle 50 which is suspended according to a combination of the result information S35 and result information S34. The result information S35 is result information on the identification of the shape of the floating particle 50. The result information S34 is result information on the identification of the size of the floating particle 50.

In the first embodiment, the scattered light receiver 20 is formed with the lens 23, the polarizing filter 22 and the scattered light detection element 21. However, the invention of the first embodiment is not limited to this. It may be configured, for example, so that the lens 23 is omitted and the scattered light Ls is detected directly by the polarizing filter 22 and the scattered light detection element 21. Alternatively, it may be configured so that the polarizing filter 22 and the scattered light detection element 21 are integrated into one body.

In FIG. 1, the scattered light receiver 20 is configured to be inclined (e.g. an inclination of approximately 30 degrees) to the travel direction of the light on the irradiation side (the irradiation laser beam L1) to detect the scattered light (the scattered light Ls) in this direction. However, the first embodiment is not limited to this. The scattered light receiver 20 may be configured to be disposed at any angle or in any direction. Alternatively, by applying another optical component which is capable of selecting light in a specific polarization direction such as a polarizing prism and a plate-type polarizing beam splitter, instead of the polarizing filter 22, the scattered light in a desired polarization direction may be guided to the scattered light detection element 21. Here, the 'desired polarization direction' indicates a polarization direction suited for identifying the shape of the floating particle 50. In the first embodiment, the 'desired polarization direction' is a direction of the polarization component which is in orthogonal relationship to the polarization component of the irradiation laser beam L1.

In the first embodiment, by the condenser lens 13, the irradiation laser beam L1 is converted to a condensed light flux. However, the invention of the first embodiment is not limited to this. If it is the structure in which the return light (the backscattered light Lbs) to the laser light irradiator 10 is obtained, the irradiation laser beam L1 emitted from the condenser lens 13 may be a light flux other than the condensed light flux.

Figure 15:
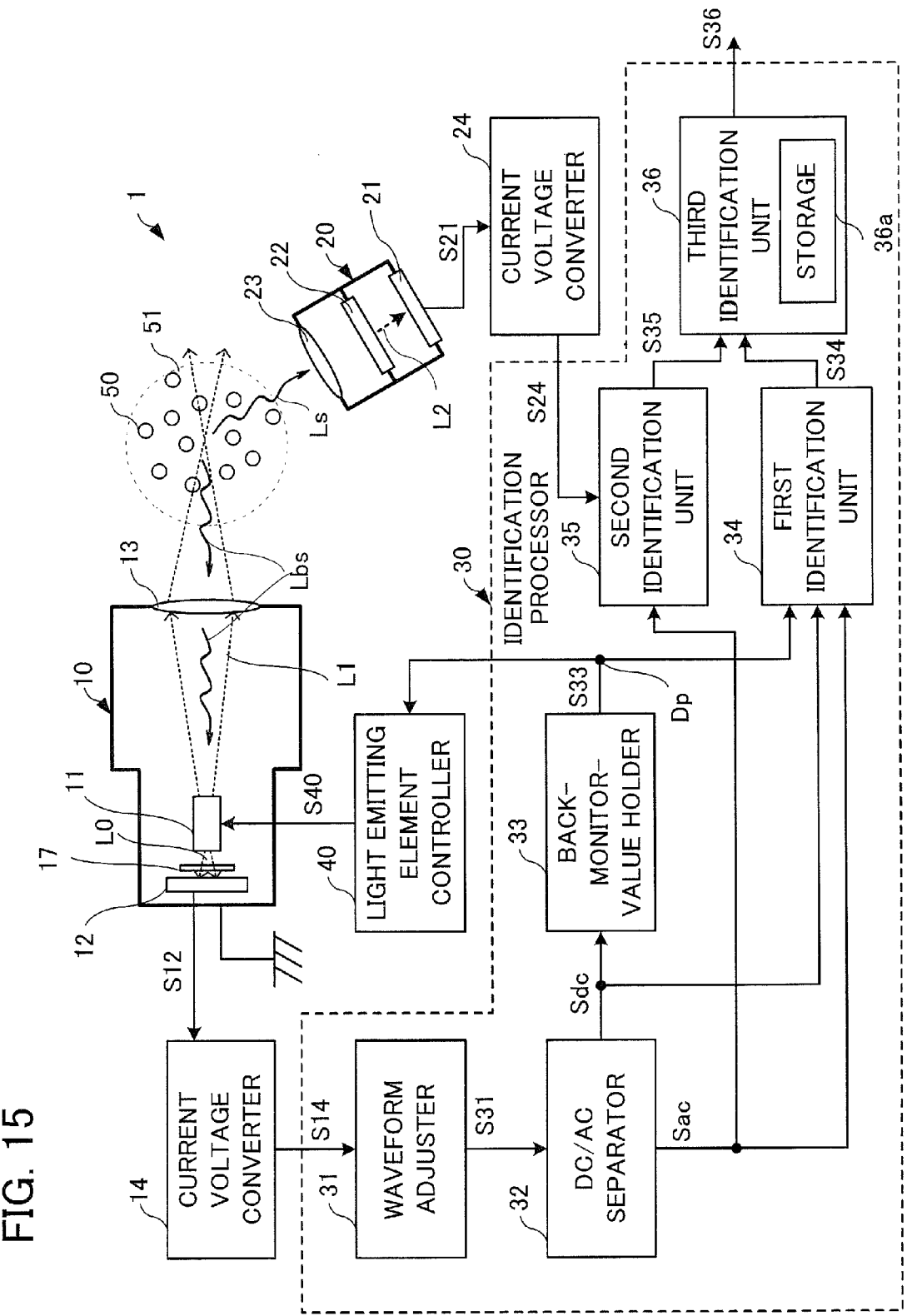
FIG. 15 is a diagram schematically showing a configuration in which a polarizing filter is added on the front side of the back-monitor-use light receiving element.

In the first embodiment, the laser light irradiator 10 may be configured such that a polarizing filter 17 is additionally disposed on the front side of the back-monitor-use light receiving element 12. FIG. 15 is a diagram schematically showing a configuration in which the polarizing filter 17 is added on the front side of the back-monitor-use light receiving element 12. The polarizing filter 17 transmits only a polarization component which is in the same relationship (i.e., parallel relationship) to the polarization component of the irradiation laser beam L1, among light which enters the back-monitor-use light receiving element 12. The irradiation laser beam L1 is irradiation light causing the backscattered light Lbs. Thus, when the floating particle 50 is irregular in shape, among the backscattered light Lbs received by the back-monitor-use light receiving element 12, a polarization component which is in orthogonal relationship to the polarization component of the irradiation laser beam L1 (the irradiation light) is cut. In other words, the back-monitor-use light receiving element 12 is capable of receiving the backscattered light Lbs including only the polarization component which is in the same relationship (i.e., parallel relationship) to the polarization component of the irradiation laser beam L1 (the irradiation light).

The scattered light Ls is made to enter the back-monitor-use light receiving element 12 as the backscattered light Lbs. The level value Ak is a level value of the AC component Sac corresponding to the backscattered light Lbs of the scattered light Ls. When the floating particle 50 is irregular in shape, the level value Ak (k is an integer) is a value including the polarization component which is in orthogonal relationship to the polarization component of the irradiation laser beam L1 and the polarization component which is in the same relationship (i.e., parallel relationship) to the polarization component of the irradiation laser beam L1.

Now, when the floating particle 50 is irregular in shape, out of the backscattered light Lbs of the scattered light Ls, a signal of a polarization component which is in parallel relationship to the polarization component of the irradiation laser beam L1 (irradiation light) is indicated by Sa. Out of the backscattered light Lbs of the scattered light Ls from the irregular-shaped floating particle 50, a signal of a polarization component which is in orthogonal relationship to the polarization component of the irradiation laser beam L1 (the irradiation light) is indicated by Spb. When the floating particle 50 is irregular in shape, the signal Sac from the scattered light which is made to enter the back-monitor-use light receiving element 12 is represented as Sac=Sa+Spb. The signal Sac is a signal of the AC component of the detection signal S31.

If no polarizing filter is included, a normalized peak value of the detection signal S24 (the value P indicating the normalized degree of shape irregularity) is represented as Sp/(Sa+Spb). When the calculation is made, the polarization component which is in orthogonal relationship to the polarization component of the irradiation laser beam L1 is included in the denominator and numerator of the expression representing the value P. For this reason, in the expression representing the value P, an error occurs due to a ratio between a polarization component which is in orthogonal relationship to an ideal polarization component of the irradiation laser beam L1 and a polarization component which is in the same relationship to the polarization component of the irradiation laser beam L1.

On the other hand, if the polarizing filter is included, a normalized peak value of the detection signal S24 is represented as Sp/Sa. Accordingly, the denominator of the expression representing the value P is the value Sa of the polarization component of the irradiation laser beam L1. The numerator of the expression representing the value P is the value Sp of the polarization component which is in orthogonal relationship to the irradiation laser beam L1. When the calculation is made, the expression representing the value P is separated into the value Sa and the value Sp. For this reason, it is possible to keep with high accuracy a ratio of the value Sp of the polarization component which is in orthogonal relationship to the ideal polarization component of the irradiation laser beam L1 to the value Sa of the polarization component which is in the same relationship to the polarization component of the irradiation laser beam L1.

In the conventional floating particle detection device (patent document 1), for identifying a shape of a floating particle, a plurality of detection optical systems was necessary on its light receiver side. These detection optical systems individually detect two polarization components of scattered light. On the other hand, the floating particle detection device 1 according to the first embodiment described above includes only the detection optical system for detecting one polarization component, and thus can achieve the simple configuration. The floating particle detection device 1 detects the presence of the floating particle or the size of the floating particle by using the return light on the light source side. The floating particle detection device 1 is capable of identifying the type of the floating particle by using results of these detections.

In the invention of the first embodiment, detection of the scattered light generated when the floating particle is irradiated with the laser beam is performed by the single scattered light receiver, and detection of the backscattered light generated when the floating particle is irradiated with the laser beam is performed by the back-monitor-use light receiving element which is a part of the laser light irradiator.

Therefore, it is possible to suppress an increase in components of the device and thus achieve simplification of the configuration of the device.

Moreover, in the invention of the first embodiment, it is possible to identify the shape of the floating particle on the basis of a result of detection of a polarization component of the scattered light generated when the floating particle is irradiated with the laser beam, to identify the size of the floating particle on the basis of the amplitude of the waveform peak caused by the floating particle among the output from the back-monitor-use light receiving element, to identify the number or density of the floating particles on the basis of the number or occurrence frequency of the waveform peaks, and to identify the type of the floating particle on the basis of results of these identifications.

Second Embodiment

Figure 16:
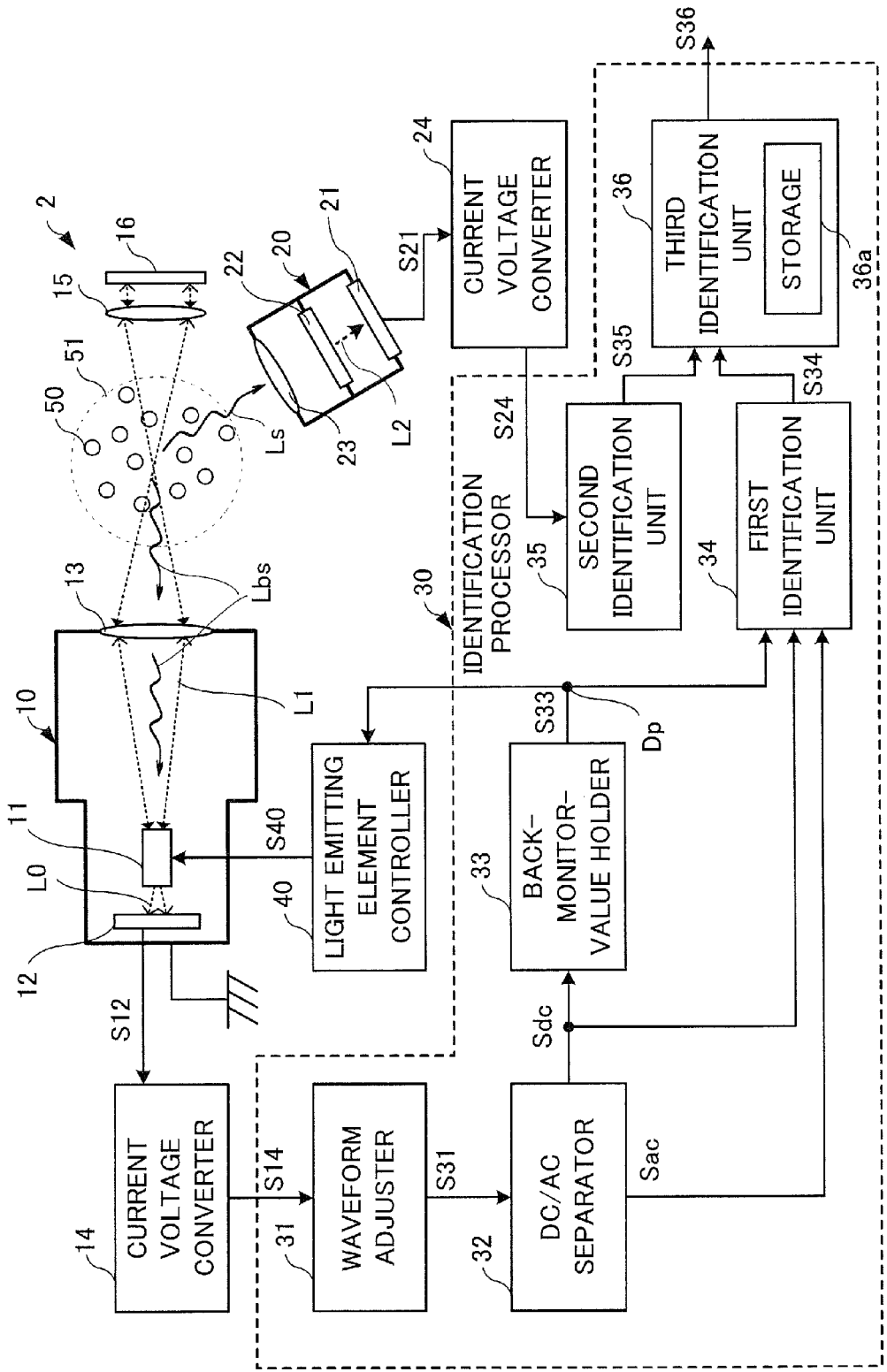
FIG. 16 is a diagram schematically showing a configuration of a floating particle detection device according to a second embodiment of the present invention.

FIG. 16 is a diagram schematically showing a configuration of a floating particle detection device 2 according to a second embodiment of the present invention. In FIG. 16, components that are the same as or correspond to the components shown in FIG. 1 are denoted by the same reference characters as the reference characters in FIG. 1, and an explanation thereof is omitted. The components that are the same as or correspond to those in FIG. 1 are the laser light irradiator 10, the scattered light receiver 20, the identification processor 30, the light emitting element controller 40 and the current voltage converters 14 and 24. In the laser light irradiator 10, the components that are the same as or correspond to those in FIG. 1 are the laser light emitting element 11, the back-monitor-use light receiving element 12 and the condenser lens 13. In the scattering light receiver 20, the components that are the same as or correspond to those in FIG. 1 are the scattered light detection element 21, the polarizing filter 22 and the lens 23. In the identification processor 30, the components that are the same as or correspond to those in FIG. 1 are the waveform adjuster 31, the direct-current/alternating-current (DC/AC) separator 32, the back-monitor-value holder 33, the first identification unit 34, the second identification unit 35 and the third identification unit 36.

The floating particle detection device 2 according to the second embodiment further includes a lens 15 and a mirror 16, and differs in this regard from the floating particle detection device 1 according to the first embodiment shown in FIG. 1. The lens 15 changes the irradiation laser beam L1 to a parallel light flux. The mirror 16 reflects the irradiation laser beam L1 which has been changed to the parallel light flux by the lens 15, and returns it to the laser light irradiator 10.

An emission edge surface of the laser light emitting element 11 and the mirror 16 form an external resonance system. The detection-target region 51 exists in the external resonance system. For this reason, the external resonance condition varies due to the floating particle 50 in the detection-target region 51. Consequently, the back-monitor-use light receiving element 12 detects fluctuations. In the second embodiment, a signal Sac and a signal Sdc obtained by using the fluctuations are supplied to the first identification unit 34. Except for this point, the second embodiment is the same as the first embodiment.

In the conventional floating particle detection device (patent document 1), for identifying a shape of a floating particle, a plurality of detection optical systems was necessary on its light receiver side. These detection optical systems individually detect two polarization components of scattered light. On the other hand, the floating particle detection device 2 according to the second embodiment described above includes only the detection optical system for detecting one polarization component, and thus can achieve the simple configuration. The floating particle detection device 2 detects the presence of the floating particle or the size of the floating particle by using the return light on the light source side. The floating particle detection device 2 is capable of identifying the type of the floating particle by using results of these detections.

In the invention of the second embodiment, detection of the scattered light generated when the floating particle is irradiated with the laser beam is performed by the single scattered light receiver, and detection of the backscattered light generated when the floating particle is irradiated with the laser beam is performed by the back-monitor-use light receiving element which is a part of the laser light irradiator. Therefore, it is possible to suppress an increase in components of the device and thus achieve simplification of the configuration of the device.

Moreover, in the invention of the second embodiment, it is possible to identify the shape of the floating particle on the basis of a result of detection of a polarization component of the scattered light generated when the floating particle is irradiated with the laser beam, to identify the size of the floating particle on the basis of the amplitude of the waveform peak caused by the floating particle among the output from the back-monitor-use light receiving element, to identify the number or density of the floating particles on the basis of the number or occurrence frequency of the waveform peaks, and to identify the type of the floating particle on the basis of results of these identifications.

Third Embodiment

Figure 17:
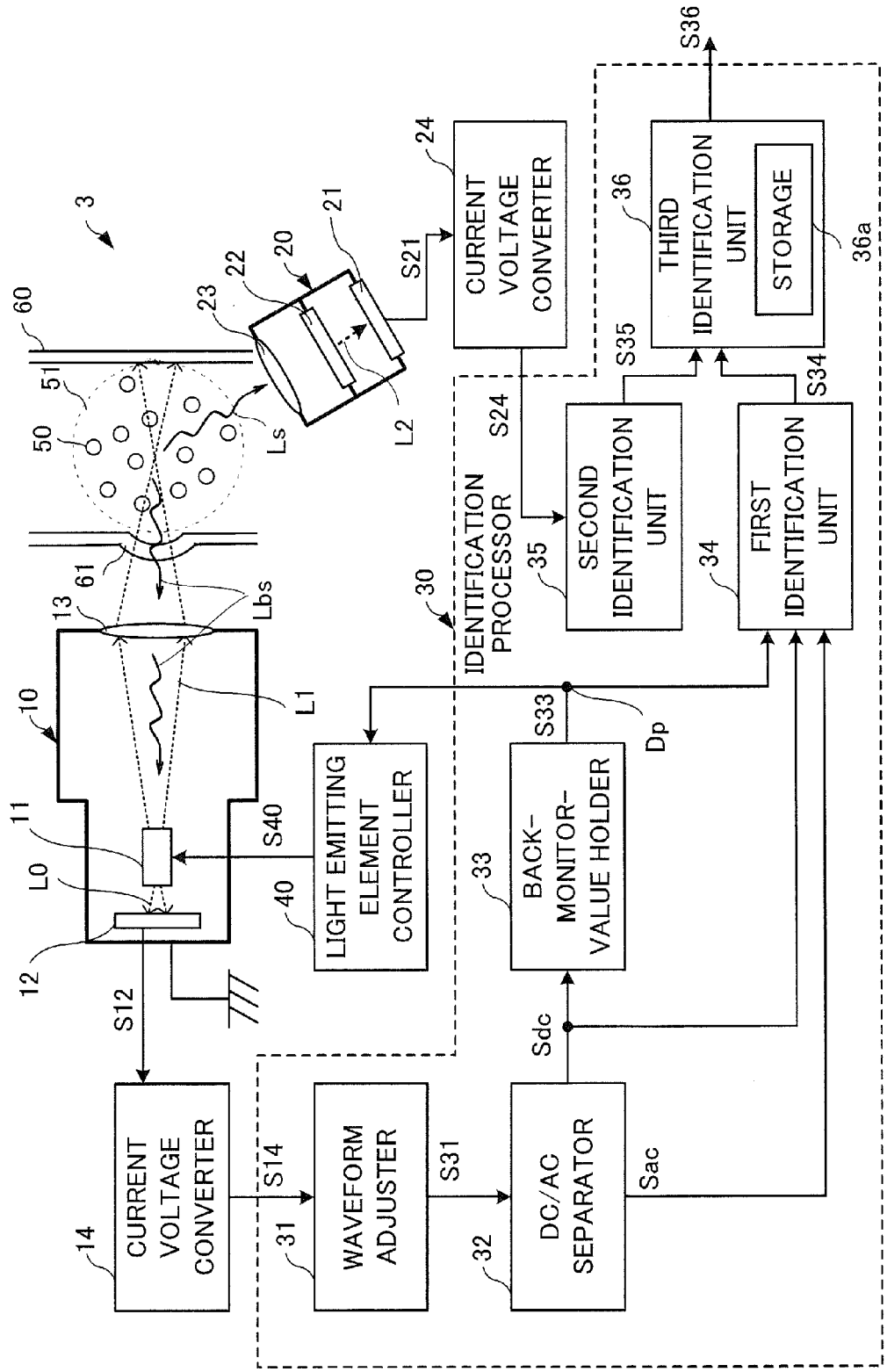
FIG. 17 is a diagram schematically showing a configuration of a floating particle detection device according to a third embodiment of the present invention.

FIG. 17 is a diagram schematically showing a configuration of a floating particle detection device 3 according to a third embodiment of the present invention. In FIG. 17, components that are the same as or correspond to the components shown in FIG. 1 are denoted by the same reference characters as the reference characters in FIG. 1, and an explanation thereof is omitted. The components that are the same as or correspond to those in FIG. 1 are the laser light irradiator 10, the scattered light receiver 20, the identification processor 30, the light emitting element controller 40, and the current voltage converters 14 and 24. In the laser light irradiator 10, the components that are the same as or correspond to those in FIG. 1 are the laser light emitting element 11, the back-monitor-use light receiving element 12 and the condenser lens 13. In the scattered light receiver 20, the components which are the same as or correspond to those in FIG. 1 are the scattered light detection element 21, the polarizing filter 22 and the lens 23. In the identification processor 30, the components that are the same as or correspond to those in FIG. 1 are the waveform adjuster 31, the direct-current/alternating-current (DC/AC) separator 32, the back-monitor-value holder 33, the first identification unit 34, the second identification unit 35 and the third identification unit 36.

The floating particle detection device 3 according to the third embodiment further includes a container 60, and differs in this regard from the floating particle detection device 1 according to the first embodiment. The container 60 is a transparent or translucent container for accommodating a liquid or gas. The container 60 may also be a transparent or translucent container provided in a flow path where a liquid or gas flows. In general, a 'container' is a container for putting things in. However, the 'container' is explained as one for limiting a liquid or gas in a certain region here. In other words, the 'container' limits a movement of a liquid or gas which contains the floating particles 50 to a region other than the region limited by the 'container'. The detection-target region 51 is a region in a liquid accommodated in the container 60. In the detection-target region 51, the floating particles 50 are present.

The floating particle detection device 3 according to the third embodiment may also include an aberration corrector 61. The aberration corrector 61 is provided in a position through which the irradiation laser beam L1 passes, in the container 60. The aberration corrector 61 corrects aberration of the irradiation laser beam L1. The aberration corrector 61 has a lens structure, for example.

Here, an explanation will be made in a case of a liquid containing the floating particles 50. The liquid containing the floating particles 50 is accommodated in the container 60. A material of the container 60 has a characteristic of transmitting the irradiation laser beam L1. The aberration corrector 61 is provided in a position of an incident surface for the irradiation laser beam L1, in the container 60. The aberration corrector 61 is formed with a three-dimensional shape. The aberration corrector 61 has a shape for correcting aberration so that the irradiation laser beam L1 can be condensed in the liquid with desired quality. Here, the 'desired quality' means the condensed light diameter, reduction of aberration, or the like which is suitable for identification of the floating particle 50 that is an detection target object. As the container 60, for example, a cylindrical-shaped hollow container, a cuboid-shaped hollow container, a polygonal-column-shaped hollow container or the like can be used. The shape of the container 60 is not specially limited. When the irradiation laser beam L1 condensed by the condenser lens 13 is transmitted through the member of the container 60, light concentration quality in the liquid deteriorates. The deterioration in the light concentration quality is caused by thickness of the container 60, a refractive index of the container 60, a refractive index of the liquid, and so on. Even if the shape of the container 60 is a simple flat surface, for example, the irradiation laser beam L1 is affected by these. The aberration corrector 61 is provided for preventing the deterioration in the light concentration quality. The shape of the light incident side of the container 60 (the shape of the aberration corrector 61) has a shape for correcting aberration so that light can be condensed with desired quality. As the aberration corrector 61, for example, a shape such as a convex-lens shape, a hemispherical shape and the like can be used.

As described above, the floating particle detection device 3 according to the third embodiment has the simple optical configuration in which a plurality of detection optical systems for individually detecting two polarization components are not needed. Moreover, the floating particle detection device 3 is capable of irradiating the floating particles 50 as the detection target objects contained in the liquid in the container 60 with the concentrated irradiation laser beam L1.

Furthermore, the floating particle detection device 3 is capable of increasing the intensity of the return light from the floating particle 50. This makes it possible to return the return light (scattered light) efficiently to the laser light irradiator 10. Therefore, the floating particle detection device 3 is capable of keeping sensitivity to detection of the floating particle 50 in the liquid large.

Except for the other points, the third embodiment is the same as the first or second embodiment described above. To the third embodiment, the various variations described in the first or second embodiment can be applied.

In the conventional floating particle detection device (patent document 1), for identifying a shape of a floating particle, a plurality of detection optical systems was necessary on its light receiver side. These detection optical systems individually detect two polarization components of the scattered light. On the other hand, the floating particle detection device 3 according to the third embodiment described above includes only the detection optical system for detecting one polarization component, and thus can achieve the simple configuration. The floating particle detection device 3 detects the presence of the floating particle or the size of the floating particle by using the return light on the light source side. The floating particle detection device 3 is capable of identifying the type of the floating particle by using results of these detections.

In the invention of the third embodiment, detection of the scattered light generated when the floating particle is irradiated with the laser beam is performed by the single scattered light receiver, and detection of the backscattered light generated when the floating particle is irradiated with the laser beam is performed by the back-monitor-use light receiving element which is a part of the laser light irradiator. Therefore, it is possible to suppress an increase in components of the device, and thus achieve simplification of the configuration of the device.

Moreover, in the invention of the third embodiment, it is possible to identify the shape of the floating particle on the basis of a result of detection of a polarization component of the scattered light generated when the floating particle is irradiated with the laser beam, to identify the size of the floating particle on the basis of the amplitude of the waveform peak caused by the floating particle among the output from the back-monitor-use light receiving element, to identify the number or density of the floating particles on the basis of the number or occurrence frequency of the waveform peaks, and to identify the type of the floating particle on the basis of results of these identifications.

The embodiments of the present invention are described above, however, the present invention is not limited to these embodiments.

DESCRIPTION OF REFERENCE CHARACTERS

1, 2, 3 floating particle detection device; 10 laser light irradiator; 11 laser light emitting element; 12 back-monitor-use light receiving element; 13 condenser lens; 14 current voltage converter; 15 lens; 16 mirror; 20 scattered light receiver; 21 scattered light detection element; 22 polarizing filter; 23 lens; 24 current voltage converter; 30 identification processor; 31 waveform adjuster; 32 direct-current/alternating-current separator; 33 back-monitor-value holder; 34 first identification unit; 35 second identification unit; 36 third identification unit; 36a storage; 40 light emitting element controller; 50 floating particle; 51 detection-target region; 60 container; 61 aberration corrector; L0 back-monitor-use laser beam; L1 irradiation laser beam; Ls scattered light; Lbs backscattered light.

What is claimed is:

1. A floating particle detection device comprising:
a laser light irradiator that includes a laser light emitting element including a front-side edge surface that emits an irradiation laser beam with which a detection-target region where floating particles are present is irradiated and a back-side edge surface that emits a back-monitor-use laser beam which travels in a direction opposite to a travel direction of the irradiation laser beam, and a back-monitor-use light receiving element disposed in a position where the back-monitor-use laser beam is incident, the back-monitor-use light receiving element generating a first detection signal according to an amount of incident light;

a scattered light receiver that selectively receives light of a predetermined polarization component among scattered light of the irradiation laser beam, the scattered light being generated when a floating particle is irradiated, thereby generating a second detection signal; and an identification processor that identifies a type of the floating particle on a basis of the first detection signal and the second detection signal;

wherein the incident light entering the back-monitor-use light receiving element includes the back-monitor-use laser beam and backscattered light travelling toward the laser light irradiator among the scattered light of the irradiation laser beam with which the floating particle is irradiated.

2. The floating particle detection device according to claim 1, wherein a fluctuation of the back-monitor-use laser beam is used for the identification of the type of the floating particle, the fluctuation being caused by entering of the backscattered light travelling toward the laser light irradiator, among the scattered light of the irradiation laser beam with which the floating particle is irradiated, through the front-side edge surface of the laser light emitting element of the laser light irradiator.

3. The floating particle detection device according to claim 1, wherein the incident light entering the back-monitor-use light receiving element includes at least one of a component entering the back-monitor-use light receiving element among the backscattered light and another component entering through the front-side edge surface of the laser light emitting element among the backscattered light.

4. The floating particle detection device according to claim 1, wherein the scattered light receiver includes:

a polarizing filter that transmits only light of the predetermined polarization component among the scattered light of the irradiation laser beam; and a scattered light detection element that receives the light of the polarization component transmitted through the polarizing filter, thereby generating the second detection signal.

5. The floating particle detection device according to claim 1, wherein the light of the predetermined polarization component among the scattered light of the irradiation laser beam is light of linear polarization having a polarization direction which is orthogonal to a polarization direction of the irradiation laser beam emitted from the laser light emitting element.

6. The floating particle detection device according to claim 1, wherein the identification processor includes a first identification unit that detects at least one of size of the floating particle and density of the floating particles, on a basis of the first detection signal generated by the back-monitor-use light receiving element.

7. The floating particle detection device according to claim 6, wherein the identification processor further includes a direct-current/alternating-current separator that separates the first detection signal generated by the back-monitor-use light receiving element into a first direct-current component which corresponds to the back-monitor-use laser beam and an alternating-current component which corresponds to the backscattered light travelling toward the laser light irradiator;

the detection of at least one of the size of the floating particle and the density of the floating particles by the first identification unit is performed on a basis of the first direct-current component and the alternating-current component separated by the direct-current/alternating-current separator.

8. The floating particle detection device according to claim 7, wherein the identification processor further includes a back-monitor-value holder that holds the first direct-current component as a second direct-current component at a predetermined time point.

9. The floating particle detection device according to claim 8, further comprising a light emitting element controller that controls driving of the laser light emitting element on a basis of the second direct-current component held in the back-monitor-value holder.

10. The floating particle detection device according to claim 8, wherein the first identification unit performs an identification of the floating particle on a basis of a result of comparison of the second direct-current component held in the back-monitor-value holder and the first direct-current component which is a direct current component presently separated by the direct-current/alternating-current separator.

11. The floating particle detection device according to claim 6, wherein the identification processor further includes:

a waveform adjuster that adjusts a waveform of the first detection signal generated by the back-monitor-use light receiving element so that an alternating-current component corresponding to the backscattered light is emphasized more than a first direct-current component corresponding to the back-monitor-use laser light; and a direct-current/alternating-current separator that separates the first detection signal adjusted by the waveform adjuster into the first direct-current component and the alternating-current component;

the detection of at least one of the size of the floating particle and the density of the floating particles by the first identification unit is performed on a basis of the first direct-current component and the alternating-current component separated by the direct-current/alternating-current separator.

12. The floating particle detection device according to claim 11, wherein the identification processor further includes a back-monitor-value holder that holds the first direct-current component as a second direct-current component at a predetermined time point.

13. The floating particle detection device according to claim 12, further comprising a light emitting element controller that controls driving of the laser light emitting element on a basis of the second direct-current component held in the back-monitor-value holder.

14. The floating particle detection device according to claim 12, wherein the first identification unit performs an identification of the floating particle on a basis of a result of comparison of the second direct-current component held in the back-monitor-value holder and the first direct-current component which is a direct current component presently separated by the direct-current/alternating-current separator.

15. The floating particle detection device according to claim 1, wherein the identification processor includes a second identification unit that identifies a shape of the floating particle, on a basis of the second detection signal generated by the scattered light receiver.

16. The floating particle detection device according to claim 6, wherein the identification processor includes:
- a second identification unit that identifies a shape of the floating particle, on a basis of the second detection signal generated by the scattered light receiver; and
- a third identification unit that identifies the type of the floating particle, on a basis of at least one of the size of the floating particle and the density of the floating particles obtained from the first identification unit, and the shape of the floating particle obtained from the second identification unit.

17. The floating particle detection device according to claim 1, further comprising a light reflection member that changes a travel direction of a laser beam which is part of the irradiation laser beam has passed through the detection-target region, to a direction toward the laser light emitting element.

18. The floating particle detection device according to claim 1, wherein the detection-target region where the floating particles are present is a region in a gas.

19. The floating particle detection device according to claim 1, further comprising a container that accommodates a liquid and is transparent or translucent,
wherein the detection-target region where the floating particles are present is a region in the liquid accommodated in the container.

20. The floating particle detection device according to claim 19, wherein the container includes an aberration corrector for correcting aberration of the irradiation laser beam, the aberration corrector being provided in a position through which the irradiation laser beam passes.

* * * * *